US012281178B2

United States Patent
Fennouri et al.

(10) Patent No.: US 12,281,178 B2
(45) Date of Patent: Apr. 22, 2025

(54) TUNING OF PORE-FORMING PEPTIDES FOR INCREASING PORE SIZE, MEMBRANE AFFINITY, STABILITY, AND ANTIMICROBIAL ACTIVITY

(71) Applicant: ADOLPHE MERKLE INSTITUTE, UNIVERSITY OF FRIBOURG, Fribourg (CH)

(72) Inventors: Aziz Fennouri, Fribourg (CH); Jonathan List, Fribourg (CH); Michael Mayer, Fribourg (CH)

(73) Assignee: ADOLPHE MERKLE INSTITUTE, UNIVERSITY OF FRIBOURG, Fribourg (CH)

( * ) Notice: Subject to any disclaimer, the term of this patent is extended or adjusted under 35 U.S.C. 154(b) by 927 days.

(21) Appl. No.: 17/278,765

(22) PCT Filed: Oct. 4, 2019

(86) PCT No.: PCT/EP2019/076974
§ 371 (c)(1),
(2) Date: Mar. 23, 2021

(87) PCT Pub. No.: WO2020/074399
PCT Pub. Date: Apr. 16, 2020

(65) Prior Publication Data
US 2022/0033527 A1     Feb. 3, 2022

Related U.S. Application Data

(60) Provisional application No. 62/742,579, filed on Oct. 8, 2018.

(51) Int. Cl.
*G01N 33/487*     (2006.01)
*C07K 14/435*     (2006.01)
*C07K 19/00*     (2006.01)

(52) U.S. Cl.
CPC ........ *C07K 19/00* (2013.01); *C07K 14/43577* (2013.01)

(58) Field of Classification Search
None
See application file for complete search history.

(56) References Cited

U.S. PATENT DOCUMENTS

| | | | |
|---|---|---|---|
| 2005/0123563 A1 | 6/2005 | Doranz et al. | |
| 2010/0069606 A1* | 3/2010 | Bangera | A61K 47/6901 977/734 |

(Continued)

FOREIGN PATENT DOCUMENTS

| | | |
|---|---|---|
| CN | 101022838 A | 8/2007 |
| CN | 104936682 A | 9/2015 |

(Continued)

OTHER PUBLICATIONS

Henning-Knechtel et al., DNA-assisted oligomerization of pore-forming toxin monomers into precisely-controlled protein channels, Nucleic Acids Res. Dec. 1, 2017;45(21):12057-12068. doi: 10.1093/nar/gkx990; US20220162692.*

(Continued)

*Primary Examiner* — Aaron A Priest
(74) *Attorney, Agent, or Firm* — Hudak, Shunk & Farine Co. LPA

(57) ABSTRACT

Pore-forming peptides or proteins modified utilizing DNA nanotechnology, which provides definition and control of pore size, an increase in stability when inserted in a lipid membrane, and membrane affinity. Chemical modifications are easily made on the compound through hybridization to the oligonucleotide attached to the peptide or protein. The compound can hybridize to a DNA template thereby defining the number of monomers assembled to a pore and thus the size of the formed pore. The DNA template can range from a unique single strand composed of multiple hybrid- (Continued)

ization sites separated by flexible linkers to a complex rigid DNA nanoconstruct, such as a DNA origami-based ring, serving as a scaffold for pore formation. Hydrophilic modification at the transmembrane segment or terminus of the peptide provides long-lived pores and keeps the compound in a membrane-spanning conformation.

21 Claims, 25 Drawing Sheets

Specification includes a Sequence Listing.

(56) References Cited

U.S. PATENT DOCUMENTS

2015/0374844 A1    12/2015  Degrado et al.
2022/0162692 A1*    5/2022  Bayley ............. G01N 33/48721

FOREIGN PATENT DOCUMENTS

JP    2018099141 A    6/2018
WO   2018068135 A    4/2018

OTHER PUBLICATIONS

Evan Spruijt, et al., "DNA scaffolds support stable and uniform peptide nanopores", Nature Nanotechnology, May 28, 2018, pp. 739-745, vol. 13 No. 8, Nature Publishing Group, London, England.
Bioinspired Materials: "National Center of Competence in Research Bio-Inspired Materials" Oct. 30, 2018, pp. 1-63, NCCR Bio-Inspired Materials c/o Adolphe Merkle Institute, Fribourg, Switzerland. ** Although this document was cited in the International Search Report it is not prior art as an incorrect date of publication was listed in the Search Report.
Anja Henning-Knechtel et al: "DNA-assisted oligomerization of pore-forming toxin monomers into precisely- controlled protein channels", Nucelic Acids Research Advance Access, Oct. 27, 2017, pp. 12057-12068, vol. 45, No. 21, Oxford University Press.
Stefan Howorka: "Building membrane nanopores", Nature Nanotechnology, Jul. 1, 2017, pp. 619-630, vol. 12, No. 7.
Evan Spruijt, et al., "DNA scaffolds support stable and uniform peptide nanopores", Nature Nanotechnology, May 28, 2018, 21 Pages, vol. 13 No. 8, Nature Publishing Group, London, England, Supplementary Information.
Langecker, M. et al., Synthetic lipid membrane channels formed by designed DNA nanostructures, Science, 338, pp. 932-936, doi:10.1126/science.1225624 (2012).
Krishnan, S. et al., Molecular transport through large-diameter DNA nanopores, Nat Commun, 7, 12787, doi:10.1038/ncomms12787 (2016).
Burns, J. R., Stulz, E. & Howorka, S. Self-assembled DNA nanopores that span lipid bilayers, Nano Lett, 13, pp. 2351-2356, doi: 10.1021/nl304147f (2013).
Burns, J. R., Seifert, A., Fertig, N. & Howorka, S. A. biomimetic DNA-based channel for the ligand-controlled transport of charged molecular cargo across a biological membrane, Nature Nanotechnology, 11, p. 152, doi:10.1038/nnano.2015.279 https://www.nature.com/articles/nnano.2015.279#supplementary-information (2016).
Spruijt, E., Tusk, S. E. & Bayley, H., Dna scaffolds support stable and uniform peptide nanopores, Nature Nanotechnology, doi:10.1038/s41565-018-0139-6 (2018).
Henning-Knechtel, A., Knechtel, J. & Magzoub, M., DNA-assisted oligomerization of pore-forming toxin monomers into precisely-controlled protein channels, Nucleic Acids Research, gkx990-gkx990, doi:10.1093/nar/gkx990 (2017).
Ke, Y., Ong, L. L., Shih, W. M. & Yin, P. Three-Dimensional Structures Self-Assembled from DNA Bricks, Science, pp. 338, 1177-1183, doi:10.1126/science.1227268 (2012).
Wei, B., Dai, M. & Yin, P. Complex shapes self-assembled from single-stranded DNA tiles. Nature 485, p. 623, doi:10.1038/nature11075https://www.nature.com/articles/nature11075#supplementary-information (2012).
Marchini, D., Marri, L., Rosetto, M., Manetti, A. G. & Dallai, R., Presence of Antibacterial Peptides on the Laid Egg Chorion of the Medfly Ceratitis capitata, Biochemical and biophysical research communications, 240, pp. 657-663 (1997).
Saint, N., Marri, L., Marchini, D. & Molle, G., The antibacterial peptide ceratotoxin A displays alamethicin-like behavior in lipid bilayers, Peptides, 24, pp. 1779-1784, doi:http://dx.doi.org/10.1016/j.peptides.2003.09.015 (2003).
Majd, S. et al., Applications of biological pores in nanomedicine, sensing, and nanoelectronics, Current Opinion in Biotechnology, 21, pp. 439-476, doi:http://dx.doi.org/10.1016/j.copbio.2010.05.002 (2010).
Montal, M. & Mueller, P., Formation of bimolecular membranes from lipid monolayers and a study of their electrical properties, Proceedings of the National Academy of Sciences, 69, pp. 3561-3566 (1972).
Stahl, E., Martin, T. G., Praetorius, F. & Dietz, H., Facile and Scalable Preparation of Pure and Dense DNA Origami Solutions. Angewandte Chemie International Edition, 53, pp. 12735-12740, doi:doi:10.1002/anie.201405991 (2014).
Burns, J. R. et al. Lipid-bilayer-spanning DNA nanopores with a bifunctional porphyrin anchor, Angewandte Chemie (International ed. in English) 52, pp. 12069-12072, doi:10.1002/anie.201305765 (2013).
Brogden, "Antimicrobial Peptides: Pore Formers or Metabolic Inhibitors in Bacteria?", Nature Reviews, Feb. 10, 2005, pp. 238-250, Nature, Iowa city, Iowa.

* cited by examiner

TUNING OF PORE-FORMING PEPTIDES FOR INCREASING PORE SIZE, MEMBRANE AFFINITY, STABILITY, AND ANTIMICROBIAL ACTIVITY

The Sequence Listing under document AMIPROVSEQUENCINGV2.txt, created Sep. 16, 2019 with 49,000 bytes is incorporated by reference.

FIELD OF THE INVENTION

The present invention relates to pore-forming peptides or proteins modified utilizing DNA nanotechnology, which provides definition and control of pore size, an increase in stability when inserted in a lipid membrane, and membrane affinity. Chemical modifications are easily made on the compound through hybridization to the oligonucleotide attached to the peptide or protein. The compound can hybridize to a DNA template thereby defining the number of monomers assembled to a pore and thus the size of the formed pore. The DNA template can range from a unique single strand composed of multiple hybridization sites separated by flexible linkers to a complex rigid DNA nanoconstruct, such as a DNA origami-based ring, serving as a scaffold for pore formation. Hydrophilic modification at the transmembrane segment or terminus of the peptide provides long-lived pores and keeps the compound in a membrane-spanning conformation. When this hydrophilic modification binds to molecules (such as a DNA oligonucleotide or a biotin for biotin/streptavidin interactions, etc) on a template on the transmembrane side then the stability of the pores further increases. The compounds can be combined with various moieties and hydrophilic modifications on the transmembrane terminus (which inserts into the lipid membrane during pore formation), with many possible attachment positions being present. The templated pore-forming peptides or proteins can also be used in the context of targeted cell killing. As cytotoxicity relates to pore size, the formation of larger pores through DNA templating allows killing cells at lower concentrations of pore-forming molecules. Targeting molecules such as folic acids (which target overexpressed folate receptors on many cancer cells) can be attached to the formed pore to add targeting properties to the pores.

BACKGROUND OF THE INVENTION

Resistive pulse sensing with nanopores makes it possible to detect, characterize and, in the case of DNA or RNA, sequence individual molecules. Most of these experiments take advantage of protein nanopores like aerolysin, *Mycobacterium smegmatis* porin A (MspA), Cytolysin A (ClyA), bacteriophage Phi29 DNA-packaging motor, Fragaceatoxin (FraC), and especially α-hemolysin (αHL). While site-directed mutagenesis enables fine-tuning the function of protein pores—such as presenting amino acid side chains with desired functional groups at precisely determined locations within the nanopore lumen—the diameter of these protein pores can only be manipulated within small limits.

The emergence of DNA nanotechnology allowed freely programmable molecular arrangement of components into complex and well-defined structures with little effort. Several groups already demonstrated self-assembled DNA pores; these constructs commonly carry hydrophobic moieties, like cholesterol, which insert into the hydrophobic bilayer, forcing the hydrophilic DNA channels into the bilayer. In a pioneering study, Henning-Knechtel et al. show templated assembly of monomers of the normally heptameric α-hemolysin protein by DNA nanotechnology to assemble 12, 20 or 26 monomers to form large pores. More recently, the group of Hagan Bayley scaffolded monomers of the polysaccharide transporter Wza, leading to stable octameric pores in lipid bilayers.

An engineered molecule designed to form a nanopore to be used for resistive pulse sensing experiments would require being long-lived: the monomers forming a nanopore need to stay in a transmembrane conformation for durations at least in the order of minutes to allow collection of enough data for analysis.

Therefore, problems to be solved by the present invention were to provide a nanopore that is both long-lived in a membrane and having a tunable diameter.

Compared to solid-state pores, protein and peptide pores are attractive for resistive pulse sensing as they are straightforward to produce in large numbers by means of biotechnology, not prone to analyte clogging and their dimensions are well defined. Their main drawback for analyzing large target molecules is the small range of available sizes with conventionally used natural pore formers or ion channel proteins. The largest of these commonly used pore is ClyA with an inner pore diameter of 3.3-3.8 nm. Engineering of the protein sequences allowed formation of slightly larger pores (4.2 nm) by forming 14-meric pores instead of the native 12-meric pores.

A possibility to form synthetically designed biological nanopores with a programmable range of diameters from 0.3 to 25 nm, would be the use of DNA nanostructures. DNA nanotechnology employs the well-defined geometry and sequence specific programmability of nucleic acids to design and fabricate nanoscaled objects. Current techniques like the DNA origami method allows to create rigid objects of up to 100 nm with almost arbitrary shapes. Such constructs were also engineered to form artificial bilayer spanning nanopores. These previously presented constructs consist of a hydrophilic channel formed by DNA and several hydrophobic moieties, typically cholesterol. These hydrophobic moieties insert into the hydrophobic part of the lipid bilayer and force the hydrophilic channel, which is made from DNA, into a transmembrane configuration. With these methods, only a limited range of pore diameters could be achieved: mostly pores with inner diameters of about 2 nm[1-5]. The DNA construct itself is permeable for ions, leading to leak currents through the constructs. Fluctuations of the DNA duplexes can lead to gating behaviour.

Recently, two groups showed nucleic acid templating of proteins or peptides[6,7]. The first study by Henning-Knechtel et al. focused on arranging a precise number of the α-hemolysin pore-forming protein monomers using well-defined, circular DNA nanostructures. DNA/α-HL hybrid nanopores composed of 12, 20 or 26 monomers were developed that result in insertions into lipid bilayers, instead of the usual heptameric α-HL nanopores. The other study by Spruijt et al. employed DNA nanostructures as scaffolds to arrange peptides derived from the octameric polysaccharide transporter Wza. It was disclosed that scaffolding the peptides turned the short-lived octameric channels (3.0 s on average at +150 mV) into stable pores that could be kept in an open state for at least an hour (between −100 and +100 mV). The size of the pores was not able to be increased beyond the natural octameric pores and templating of smaller assembles did not lead to improved lifetimes.

Henning-Knechtel et al. showed that it is possible to tune the diameter of α-hemolysin nanopores, however, the synthesis and modification of such large protein monomers is not easy and expensive. The invention presented here takes advantage of the small size of pore-forming peptides that can be easily modified and synthesized in large scale by peptide synthesis companies. According to our knowledge, no one has been able to achieve the construction of a peptide-nanopore both being long-lived in a membrane and having a tunable diameter at the same time.

WO2016/144973 relates to compositions and methods based on a fast, efficient chemical reaction for conjugating a pore-forming protein, such as α-hemolysin, to a biomolecule, such as antibodies, receptors, and enzymes, such as DNA polymerase, and the use of such pore-forming protein conjugates in nanopore devices and methods.

SUMMARY OF THE INVENTION

In view of the above, the art still needs an easily modifiable pore-forming peptide or protein that can be produced having a variable pore size, relatively high affinity to a membrane and long life or stability. Such tunable pores are also desirable for cell killing applications as many pore-forming peptides display antimicrobial activity.

These needs and others are met, and the problems of the prior art are solved by the hybrid pore-forming compounds described herein. Natural pore-forming compounds are provided by attaching nucleic acid oligonucleotides to a peptide or protein on one or both of the N-terminus and C-terminus of the peptide or protein.

In one embodiment the compound includes DNA oligonucleotides, containing binding regions covalently attached to the N-terminus of the peptide, such as ceratotoxin A (CtxA). The combination allows for straightforward attachment of chemical modifications on the compound through hybridization to the oligonucleotide. Attachment of a membrane binder, for example cholesterol, via a cholesterol-modified oligonucleotide provides higher membrane affinity and increased pore-forming activity. The DNA-peptide can hybridize a single stranded DNA template, defining the number of monomers assembled to a pore—from 3 to more than 40 peptide monomers—as well as the size of the formed pore.

In a further embodiment, the hybrid pore-forming compound is provided with a hydrophilic segment or hydrophilic tail, such as a DNA strand consisting of a poly-thymine strand, that is bonded to C-terminus of the peptide. After insertion of the peptide from the cis side of the bilayer, the hydrophilic tail stays on the trans side of the membrane and keeps the peptide in a membrane-spanning conformation, leading to long-lived pores. For comparison purposes, native CtxA pores showed lifetimes of less than one second in experiments, whereas hybrid pore-forming compounds with a hydrophilic DNA tail were stable for up to many minutes. The addition of a templating structure with the desired size on the trans side of the bilayer could hybridize to the hydrophilic DNA tail, yielding a pore templated from both sides, which further increased the stability of the pores. Pores are usually optimized for fast and easy insertion into the membrane, and therefore addition of a charged and hydrophilic DNA oligonucleotide to the transmembrane segment of the peptide would be counter-intuitive as it would impede insertion into the hydrophobic membranes. In fact, it does reduce the frequency of pore insertion but leads to the more important feature of longer-lived pores as described above.

In another embodiment, the pore-forming compounds are templated by a complex rigid DNA nanoconstruct. In particular DNA origami-based rings are disclosed which serve as a scaffold to the pore formation. While single stranded templates with a large number of attachment sites are difficult to generate, the origami method allows straightforward addition of many attachment sites. The number of compound binding sites can be specifically chosen to form pores having a desired diameter, especially for pores with large diameters. Other functional moieties like hydrophobic cholesterol can be attached at desired positions on the origami construct. Formation of pores with large conductance are provided. The stability of the pores was significantly better than for native peptide pores.

The adaptability of the hybrid pore-forming compounds allows combination with affinity moieties and additional C-terminus hydrophilic modifications. The modular origami scaffolding offers more possible attachment positions for functional moieties as compared to a strategy employing one or a few template strands at geometrically well-defined positions.

In an additional embodiment, the templated pore-forming compounds are used to kill cells at lower concentrations of pore-forming molecules (theoretically one sufficiently large pore may be enough to kill a cell), by forming larger pores compared to the native pore-forming compounds. Moieties can be added to specific positions on the templated pores to target defined cells such as pathogen cells or cancer cells.

The compounds are directly synthesized by peptide synthesis companies with the DNA oligonucleotide attached (ssDNA-CtxA) or containing an azide group (Azide-CtxA) on its N-terminus that reacts via click-chemistry to dibenzocyclooctyne (DBCO)-containing oligonucleotide. CtxA with a hydrophilic tail is formed from ssDNA-CtxA modified with an azide group on its C-terminus (ssDNA-CtxA-Azide) or with a Azide-CtxA having a thiol group on its C-terminus (Azide-CtxA-Thiol). ssDNA-CtxA-Azide and Azide-CtxA-Thiol then react with an excess 12T-DBCO or 12T-maleimide to form ssDNA-CtxA-12T.

Therefore, in one embodiment a hybrid pore-forming compound is disclosed, comprising a pore-forming peptide or protein having a first terminus and a second terminus, wherein a first oligonucleotide is linked to the first terminus, wherein the first oligonucleotide is derived from DNA, RNA, LNA, BNA, or PNA, wherein a first functional moiety is linked to the second terminus, and wherein the first functional moiety is hydrophilic.

In a further embodiment, the second functional moiety of the compound is linked to a second oligonucleotide that is hybridized to the first oligonucleotide bonded to the first terminus of the peptide, wherein the second oligonucleotide is derived from DNA, RNA, LNA, BNA, or PNA, wherein the second functional moiety is a hydrophobic membrane binder, receptor, drug molecule, antibody, aptamer, metabolite, or fluorescent marker.

In an additional embodiment, the hydrophobic membrane binder is present and comprises a cholesterol moiety.

In another embodiment, the first functional moiety of the compound bonded to the second terminus of the peptide is a third oligonucleotide or fluorophore wherein the third oligonucleotide is derived from DNA, RNA, LNA, BNA, or PNA.

In a further embodiment, a template strand having a plurality of, preferably 4, 6, 8, or 12, complementary hybridization sites is hybridized to a portion of the first oligonucleotide linked to the first terminus.

In an additional embodiment, a plurality of the pore-forming peptides or proteins are present with each first oligonucleotide linked to the first terminus hybridized to the template strand, such that the compound forms a larger pore.

In another embodiment, a plurality of the pore-forming peptide or proteins are present with each first oligonucleotide linked to the first terminus hybridized to the template strand such that the compound has a tetrameric, hexameric, octameric or dodecameric pore conformation.

In a further embodiment, the pore-forming peptide is present and is Ceratotoxin A (CtxA).

In an additional embodiment of the compound, the first functional moiety is the third oligonucleotide, and wherein a second membrane binder is linked to the third oligonucleotide to aid in stabilizing a pore formed by the compound.

In another embodiment, the peptide or protein is functionalized differently at the first terminus as compared to the second terminus.

In a further embodiment, a method for forming the hybrid pore-forming compound as described in an of the above paragraphs is disclosed, comprising the steps of: obtaining i) the pore-forming peptide or protein, ii) the first oligonucleotide and iii) the first functional moiety; and forming the pore-forming compound by self-assembly of i), ii), iii).

In an additional embodiment, the method further includes reacting in solution the template strand having a plurality of complimentary hybridization sites with an excess of the pore-forming compounds comprising the i), ii), iii); removing excess unreacted pore-forming compounds, preferably by high pressure liquid chromatography.

In another embodiment, the method further includes the step of hybridizing the first oligonucleotide to the second oligonucleotide, wherein the second oligonucleotide is present in an excess amount as compared to the first oligonucleotide.

In a further embodiment, a membrane is disclosed, comprising a substrate and the compound according to any of the above-described configurations, wherein the compound provides a pore between a first side of the substrate and a second side of the substrate.

In an additional embodiment the compound according to any of the above description is provided, wherein an extended, preferably rigid, nucleic acid nanostructure serves as a template for assembling a plurality of, preferably 20 or 40, pore formers into a pore, wherein the nucleic acid nanostructure preferably contains the second functional moiety directly attached thereto, and wherein the nucleic acid nanostructure is preferably a DNA origami structure or a single stranded tile assembly or a RNA origami structure.

It is to be understood that the invention encompasses all possible combinations of the embodiments described herein.

BRIEF DESCRIPTION OF THE DRAWINGS

The invention will be better understood and other features and advantages will become apparent by reading the detailed description of the invention, taken together with the drawings, wherein:

FIG. 15A Commercially synthesized ssDNA-CtxA; FIG. 15B ssDNA-CtxA obtained after an overnight click chemistry reaction between azide-CtxA and DBCO-ssDNA; FIG. 15C ssDNA-CtxA-12T obtained after an overnight click chemistry reaction between commercially synthesized ssDNA-CtxA-azide and a 12T-DBCO oligonucleotide; FIG. 15D ssDNA-CtxA-peg4-12T obtained after an overnight click chemistry reaction between commercially synthesized ssDNA-CtxA-azide and a 12T-peg4-DBCO oligonucleotide; FIG. 15E ssDNA-CtxA-12T obtained after an overnight click chemistry reaction between azide-CtxA-Thiol and a DBCO-ssDNA. The resulting ssDNA-DNA-CtxA-Thiol later reacted overnight with a 12T-maleimide oligonucleotide via a thiol-maleimide reaction; FIG. 15F ssDNA-CtxA for the origami structure experiments obtained after an overnight click chemistry reaction between azide-CtxA and a DBCO oligonucleotide; and FIG. 15G Double-labelled ssDNA-CtxA for the origami structure experiments obtained after an overnight click chemistry reaction between azide-CtxA and an oligonucleotide possessing two DBCO moieties.

DETAILED DESCRIPTION OF THE INVENTION

Figure 1:
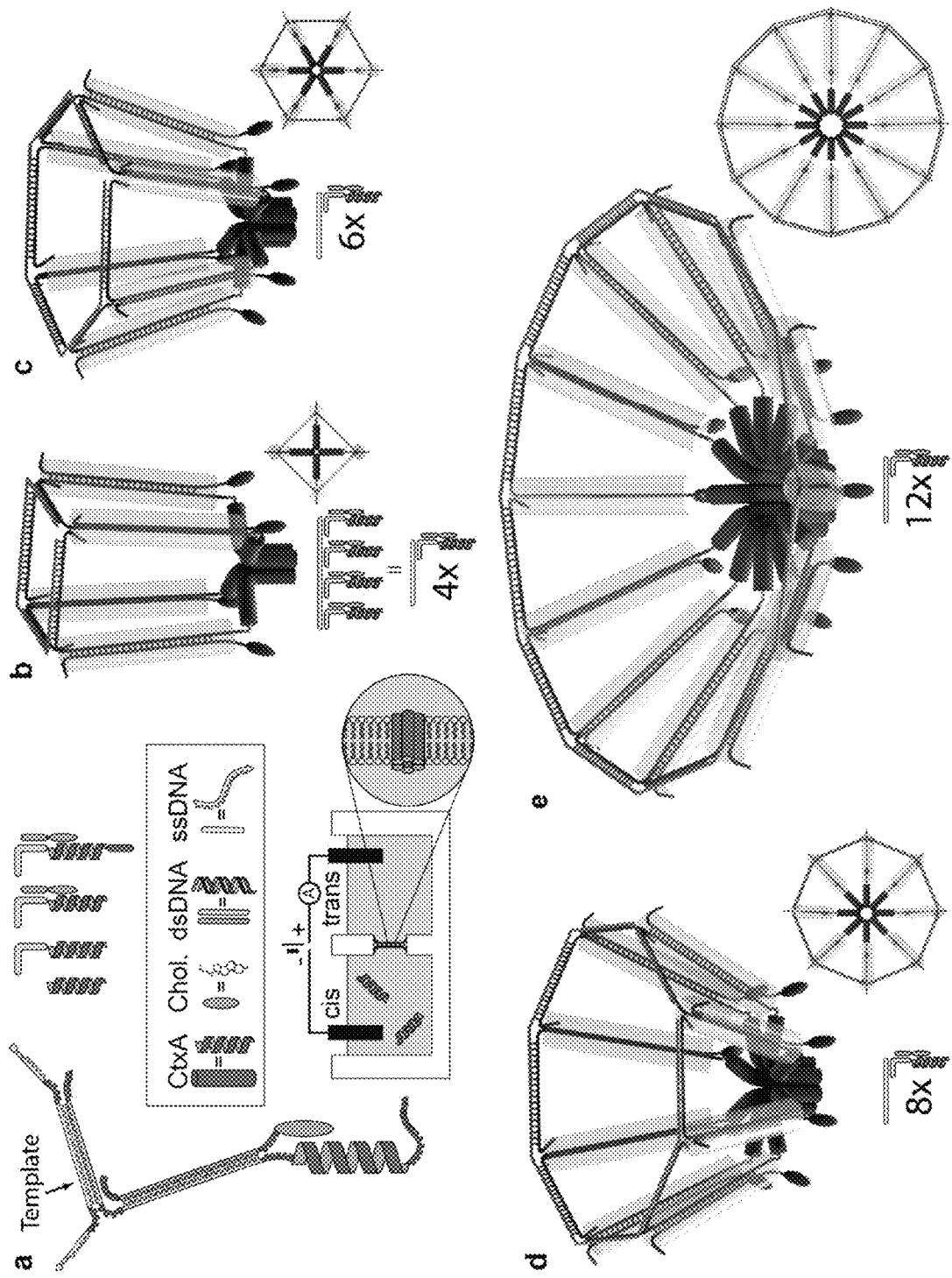
FIG. 1 illustrates a schematic representation of DNA-assembled peptide pores with programmable pore size, (a) Assembly scheme mediated by DNA hybridization with a schematic representation of the planar lipid bilayer setup used to record the pore-forming activity and single channel conductance of CtxA and of template-assembled versions of CtxA-DNA. The pore-forming peptide CtxA bears on its N-terminus a covalently attached single stranded DNA with two domains. The terminal domain binds to a template strand that presents 4, 6, 8 or 12 complementary hybridization sites. An additional DNA strand binds to the compound, carrying a hydrophobic moiety for increasing the membrane affinity. An additional hydrophilic poly-thymine segment is bonded to C-terminus of the peptide to keep the peptide in a membrane-spanning conformation, leading to long-lived pores. Four thymine bases, acting as flexible linkers, separate the DNA segments. (b-e) Schemes, projections and top views of possible special arrangements of (b) a tetrameric, (c) a hexameric, (d) an octameric pore or (e) a dodecameric pore, with fully occupied template strands containing four, six, eight or twelve binding sites for the CtxA-DNA monomers.

The invention encompasses hybrid pore-forming compounds comprising various functional groups that allow tailoring of pore size, stability and membrane affinity, among other benefits. The hybrid pore-forming compound comprises a peptide or protein having covalently attached nucleic acid oligonucleotides on both termini of the peptide or protein. Methods for making hybrid pore-forming compounds are straightforward. Many advantages are provided by the hybrid pore-forming compounds of the invention.

One particular advantage of the invention is the straightforward attachment of chemical modifications. The compounds presented here do not require further chemical synthesis and can be produced from off the shelf components.

In one embodiment, cholesterol is linked to the construct as a hydrophobic moiety to increase the affinity of the compound to a lipid bilayer of a membrane. Pore formation is observed at concentrations more than ten times lower than in absence of the cholesterol. The result was achieved without changing the peptide sequence which is one way to increase the potency of an antimicrobial peptide. However, if desired, peptide sequence can be modified as well.

Other modifications can be accomplished through hybridization to DNA strands with, by way of nonlimiting example, attached fluorescent markers, drug molecules, receptors, antibodies, aptamers, metabolites, etc. These modifications can be useful for drug delivery as well as targeted cell killing.

Modification of the peptide or protein by covalently attaching ligands to specific sites allows for the creation of biosensors. Such sensors based on resistive pulse sensing allow the detection of specific target molecules. Due to the modularity of the invention, additional functionalizations are straightforward to add or exchange.

An additional advantage provided by the hybrid pore-forming compounds is an increased lifetime of pores from peptides forming short-lived channels. Long-lived pores are required for resistive pulse sensing in order to allow collection of enough data for subsequent analysis. By providing hybrid compounds having long-lived pores efficiency of the molecule to kill pathogens cells or for drug delivery is increased.

As described herein, a single stranded DNA on the part of the peptide that is inserted into the membrane, which successfully increases the time during which the peptide is in a transmembrane conformation, namely from tens of milliseconds up to a few seconds or even several minutes.

Another important advantage of the compounds is the tailored pore size obtained by using DNA templates. The DNA template can range from a unique single strand composed of multiple hybridization sites separated by flexible linkers to complex rigid DNA nanoconstructs, such as a DNA origami-based ring, serving as a scaffold for pore formation. Rigid, large nanostructures used as templates, like the demonstrated origami ring, enable the formation of drastically larger peptide pores. Disclosed herein are simple "one pot" assembly of template structures with a large number of peptide monomer binding sites. The relatively rigid template disclosed leads to more stable peptide pores, as compared to a flexible template from double stranded DNA.

The compounds of the present invention offer specific benefits for resistive pulse sensing. For example, stable pores are provided, wherein pores are stable general for several minutes. Data analysis is impractical if in addition to translocation events, current fluctuations are caused by changes in the pore size. Increased affinity eases the formation of single pores. DNA assemblies allow simple tuning of the pore diameter and large pore diameters. Larger pores enabled by the compounds of the invention can be utilized to analyze larger target molecules.

The compounds of the invention also offer various benefits for targeted cell killing and drug delivery. The compounds are pore formers with increased affinity and are active at low concentrations. Pathogen-specific binding moieties, such as receptor binding moieties, antibodies, aptamers, etc. allow targeting selected cells, such as pathogen or other target cells. DNA assemblies in general allow for combination of several different binding motifs and stimulus response compounds with little effort. The compounds are useful for applications such as delivering macromolecules, such as siRNA, DNA, proteins, carbohydrates, etc., wherein minimum pore sizes are required, larger than the analyte size. Larger pores are also more efficient in killing cells because they disrupt cellular homeostasis.

The compounds of the present invention take advantage of the barrel-stave assembly mechanism of a pore-forming peptide, such as CtxA, to a pore, which is advantageous because various peptides such as CtxA are intrinsically able to form pores from a wide range of number of monomers and pore diameters.

When a peptide is used to create the compound that has an alpha-helical structure, such as CtxA, design flexibility is present for the assembly and reconfigurations, which can add functionality in order to stabilize the pores, for example. Typically, for instance in natural ion channel proteins, alpha helical proteins are more flexible and have more functionality than pores made from beta-sheet structures.

The compounds take advantage of a peptide that can be modified on its terminus, one or both of its C-terminus and N-terminus depending on the peptide utilized, without impeding its ability to self-assemble into well-defined pores. The C-terminus modification can be orthogonal in terms of chemical reactivity to the modification on the N-terminus, which means that both ends can be modified and functionalized differently with selective chemical reactions.

In an embodiment where the C-terminus modification of the peptide includes a thiol group (—SH), the compound is incorporated more readily into a membrane than a native peptide, such as CtxA, and assembles to pores, which demonstrates that the incorporation can be facilitated and controlled.

Chemical reactions of physical interactions of chemicals or reagents with the C-terminus of a peptide, such as CtxA, on the trans side of the membrane, i.e. the side opposite to the cis side where the compounds were added, can add functionality and stabilize the pores.

The hybrid pore-forming compounds take advantage of peptides that can self-incorporate into lipid or polymer membranes. Combination with a membrane is quite practical as methods for reconstitution into the membranes are not necessary.

When peptides such as CtxA are utilized, advantage of voltage-dependent incorporation can be used to form pores on demand, which also can be switched off on demand.

It is also been demonstrated herein that templating increases the local concentration of pore-forming peptides and therefore the probability of forming pores. This effect biases the assembly towards pores with large diameters. The compounds designed with a spacer strand, template strand, and short, flexible thymidine regions between these segments enables self-assembly of intended pore sizes reducing steric problems. Alternatively, neutral PEG linkers can be inserted. This is no small task since many alternative designs for templating may have steric constraints, low yield of complete assemblies and assemblies of inactive pores, etc.

The open design of the compound in a scaffold makes it possible to template and assemble pores without adding to the electrical resistance of the pore.

The assembly of pores can occur either before the experiments combined with purification of assembled pores or pore assembly can be carried out in situ by step-wise addition of the various components and molecules for the assembly. This flexibility in use of the molecules is advantageous to mitigate possible issues of limited solubility of either the individual components or the full assembly. Sequential, in-situ assembly from one or both sides of the membrane) also makes it possible to assemble pores with complex functionality.

For example, various pore-forming peptides are suitable for use in the present invention. Examples include, but are not limited to, ceratotoxin A, alamethicin, MelP5, melittin, magainin, cecropin, etc., or any synthetically evolved variant of these peptides. Preferably, pore-forming peptides that do not contain post-translational modifications or unnatural amino acids can be used, as they are simple to synthesize and to modify chemically to attach the DNA oligonucleotides.

Oligonucleotide can be made of nucleotide sequences including but not limiting to DNA, RNA, PNA, LNA, BNA, as well as unnatural nucleic acids. N-terminus oligonucleotides devoid of spacer region could be used, although the template should have a different geometry to account for steric hindrance. Such templates could present longer linkers between each hybridization site, while presenting hydrophobic moieties, receptors, etc. directly to the membrane surface. In another variant, multiple pore-forming peptides could bind to one oligonucleotide, allowing to multiply the number of monomers in a pore while keeping the template strand short.

The moieties on the spacer strand can be anchoring moieties such as diacyl chains, cholesterol, receptor-binding agents, aptamers, antibodies, metabolites, etc. These moieties can also be elements enhancing the detection of the construct like fluorescent dyes, proteins (or genes encoding for them) or aptamers, metabolic nanoparticles, radioactive markers, quantum dots, etc.

Pore formation and disassembly can be triggered by chemical, mechanical, light or other signals mediated by the DNA hybridization (toehold mediated strand displacement, light-switchable bases, aptamers, etc).

C-terminus moieties can be added to obtain long-lived pores. These moieties are hydrophilic or become hydrophilic once reaching the trans side of the membrane (for example due to pH change). These groups can be oligonucleotide sequences (DNA, RNA, PNA, LNA, BNA, as well as unnatural nucleic acids), amino acids or any other hydrophilic group (thiol, azide, biotin, etc.). The anchoring can also be realized by templating the pore-forming peptides on the trans side of the membrane.

The membrane can be a lipid membrane (phospholipid membrane, archaea membrane, etc.), a synthetic membrane (block copolymer, etc.), can be charged, uncharged or zwitterionic. The pore can also be employed for forming solid-state hybrid pores. Therefore, the pore is inserted into an existing solid-state nanopore to change its properties.

Here we describe a modular DNA-assembly system based on Ceratotoxin A (CtxA) peptides, for increased membrane affinity, geometrical arrangement of monomers and increased pore lifetime. Like alamethicin, the 36-amino acid peptide CtxA forms short, barrel-stave pores that increase or shrink in diameter as a consequence of association or dissociation of peptide monomers. To this end, we covalently link ssDNA to the N-terminus of CtxA peptides for hybridization of complementary oligonucleotide sequences.

Linking the peptide-DNA hybrid to DNA-coupled hydrophobic moieties increases membrane affinity. By adding a templating DNA strand with a defined number of binding sites, we bias the pore diameter towards 4-, 6-, 8- or 12-mer assemblies. We demonstrate that the introduction of a hydrophilic DNA domain on the C-terminus side of CtxA, part that is thought to insert into the lipid bilayer[1], stabilizes the hybrid monomers in a bilayer-spanning conformation. This modification turns short-lived CtxA pores with dynamically fluctuating diameters into long-lasting pores with well-defined diameters, which could be beneficial for sensing applications.

One feature of this construct is the absence of solid, ion-blocking structures, similar to the large αHL cap domain containing a vestibule. In contrast, the assembly we present is a short membrane-spanning channel, geometrically arranged by a loosely packed, open DNA structure, that circumvents additional contributions to resistance from a vestibule or a tightly packed templating structure. Additional distinct advantages of this minimalistic design of an artificial ion channel are the use of solid-phase synthesis of all components with the potential for large-scale production and the possibility to modify the sequence and number of amino acids of the peptide at any position with great flexibility for high-throughput screening. DNA-assembled peptide pores could also be used for applications other than sensing, such as drug delivery or targeted killing of pathogens.

Results and Discussion

Assembly of CtxA-DNA hybrid constructs. We design a new peptide-DNA hybrid based on the 36-amino acid peptide CtxA. A 55-base long ssDNA oligonucleotide is attached with its 5' end to the N-terminus side of the peptide, as shown in FIG. 1. Its sequence consists of two parts: a spacer region and a template-binding domain. Flexible linkers consisting of four thymine (T) bases connect all domains of the construct. A spacer strand hybridizes to the 25-nucleotide-long spacer region to form a rigid duplex. To increase its affinity to the lipid membrane, this spacer strand is modified with a cholesterol moiety on its 3' end, henceforth referred to as the cholesterol strand. The template-binding region composed of 18 nucleobases allows binding of the peptide-DNA hybrid to a single stranded DNA template with four, six, eight or twelve hybridization sites, separated by linkers of four thymine bases.

To obtain a more rigid and more defined DNA template, we constructed a ring-shaped origami structure with a diameter of 33.4 nm (inner diameter 20.6 nm). The ring was formed by bending the DNA helices to a circle. A 82×15×11 nm block structure is connected to the ring. The block does not serve the pore assembly but uses up the remaining scaffold to avoid an influence of a large single stranded DNA loop in close vicinity to the pore. 20 staples distributed on the bottom side of the ring carry extensions, ready to hybridize DNA conjugated peptides with a 20 nucleotide-long complementary attachment sequence (instead of the 55-base-long sequence of the other design). As a 20-meric peptide would form a much smaller pore of approximately 8.7 nm diameter, linkers are required. Therefore, peptide-DNA conjugates are hybridized in a distal conformation to the structure with the connecting DNA duplex acting as a 6.1 nm linker between origami structure and peptide. Two additional thymine bases were inserted on both sides of this double stranded attachment, serving as flexible linkers. To further avoid steric and electrostatic repulsion of the double stranded DNA linkers that might impede peptide pore assembly, we connected the peptide via an uncharged PEG linker to the attachment oligonucleotide. Alternatively, a strand carrying two reactive DBCO groups attached via a PEG linker was used to form up to 40-meric peptide pores.

Similar to the previously described design, additional functional moieties can easily be attached via staple extensions. We added eight further extensions with an orthogonal attachment sequence to the bottom of the ring that can carry cholesterol moieties to increase the membrane affinity of the origami structures to the membrane.

We use the CtxA peptide for this study as pores assembled from small peptides have attractive characteristics such as forming barrel-stave pores with well-defined conductance levels, and forming channels with a pore length ≤5 nm, potentially increasing the resolution of sensing applications. Its low molecular weight allows large-scale synthesis of the peptide as well as chemically functionalizing the peptide. Moreover, as the peptide is positively charged, it readily binds stronger to the negatively charged outer membranes of many pathogens compared to mammalian cells. This feature makes CtxA-based pore assemblies attractive for targeted cell killing applications FIGS. 1b-e illustrate the loose and open molecular design of the DNA-assembled peptide pore we designed. Ions can flow between the strands of the DNA-based scaffold with the advantage that the scaffold does not significantly increase the access resistance to the transmembrane segment of the pore. This design focuses the voltage drop to the membrane-spanning peptide part of the pore rendering it sensitive to conductance changes and thus increasing the signal to noise ratio for applications such as resistive pulse sensing.

Figure 2:
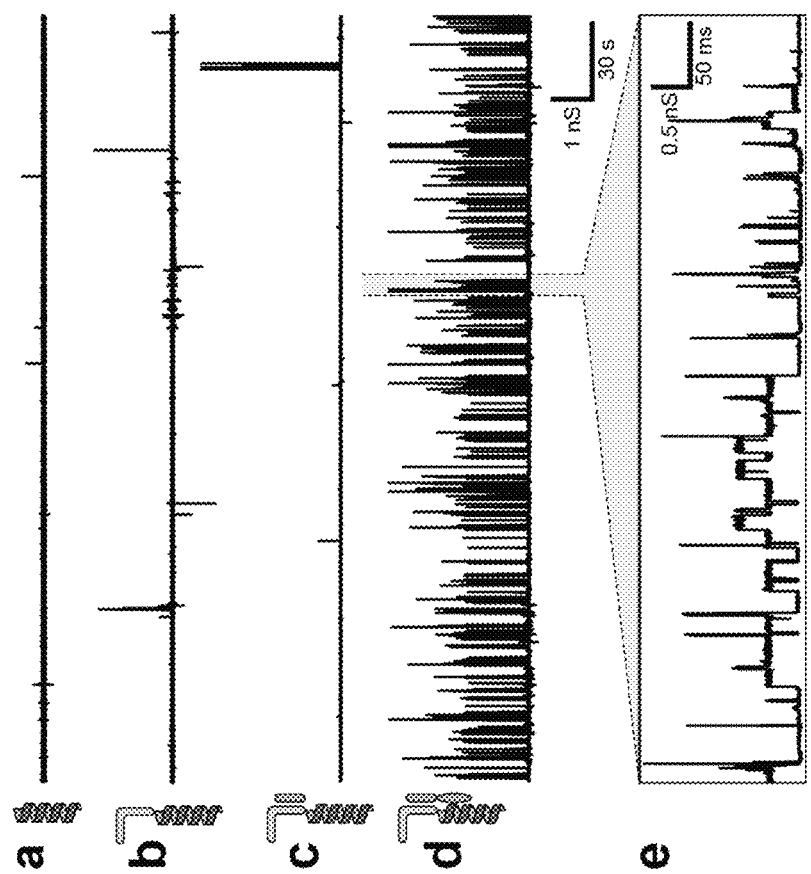
FIG. 2 illustrates increased pore-forming activity of CtxA-DNA after addition of a cholesterol strand. Experiments at 5 nM peptide concentration with (a) native CtxA, (b) ssDNA-CtxA and (c) dsDNA-CtxA did not exhibit frequent pore formation. (d) Strongly increased pore formation occurs for Chol-dsDNA-CtxA carrying a cholesterol moiety, which increases the affinity to the lipid membrane. (e) Expanded view of the current recording in (d) showing stepwise current fluctuations typical of native CtxA. All recordings are performed at an applied potential difference of +180 mV.
Figure 3:
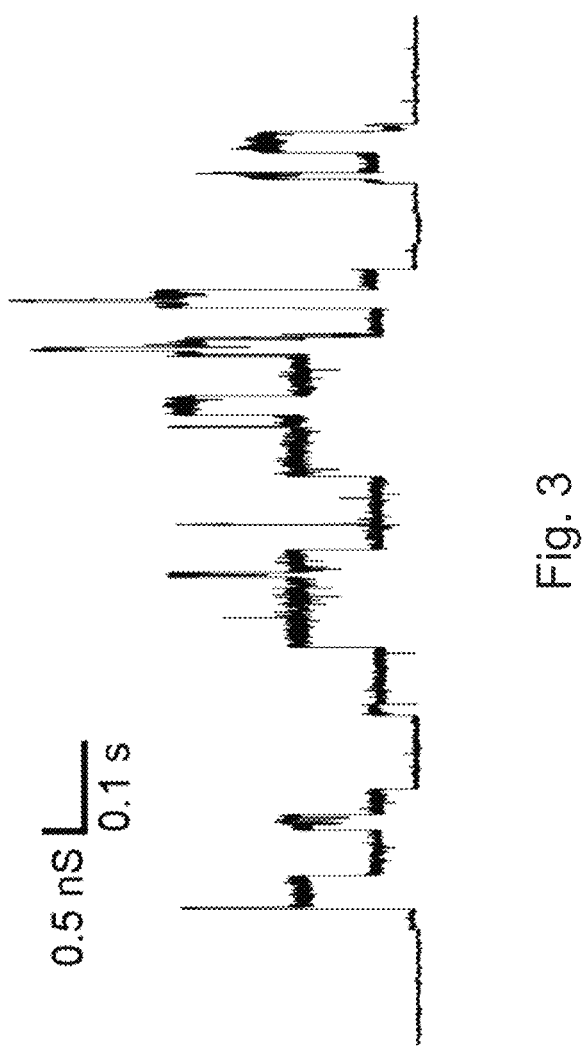
FIG. 3 displays a conductance versus time recording of the typical pore-forming activity of native CtxA. The recording shows well-defined, stepwise increases and decreases of the conductance that correlate with the uptake or release of a peptide monomer from the assembled pore. All recordings were performed at an applied potential difference of +180 mV and in presence of 20 nM peptide.
Figure 4:
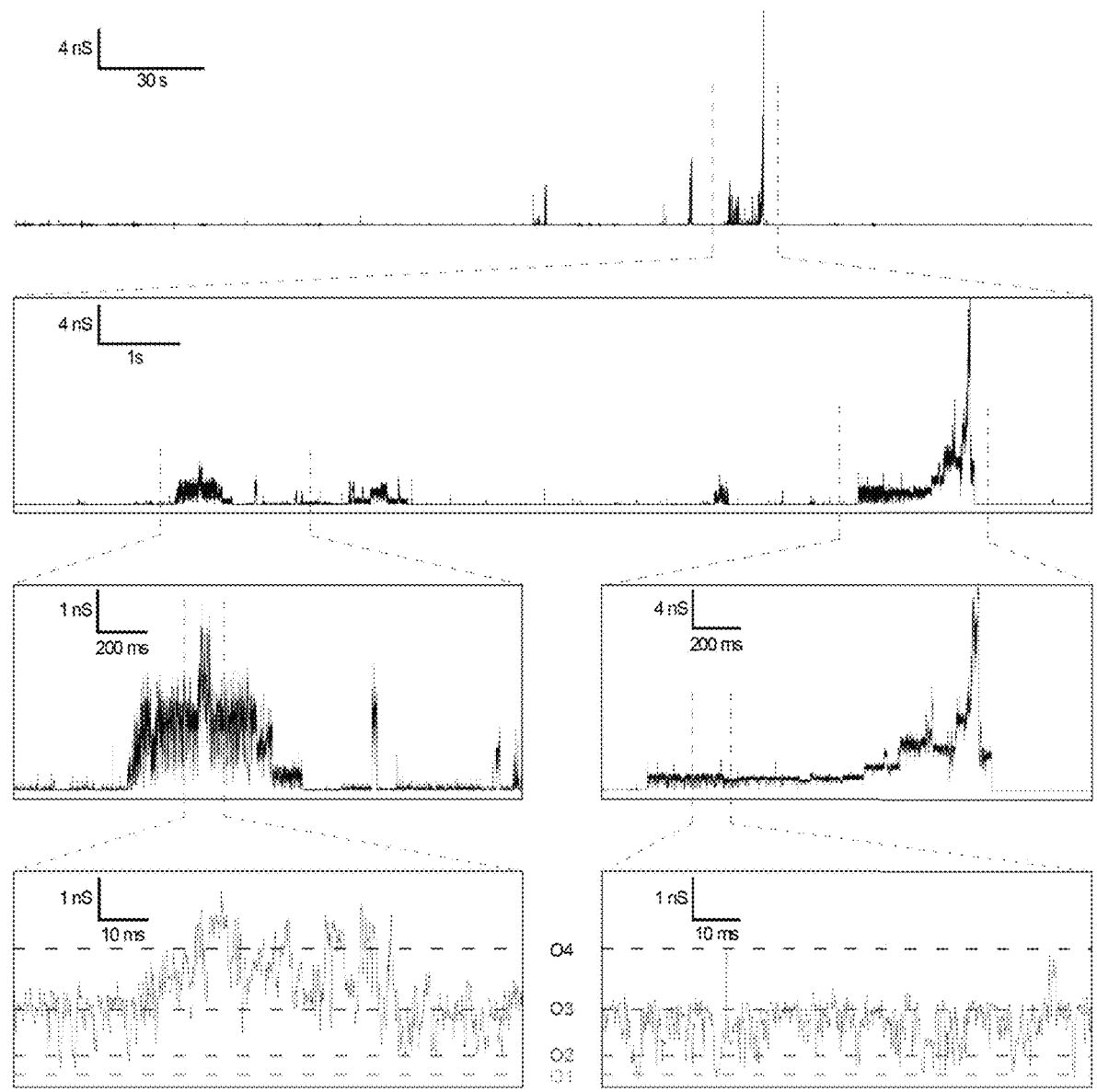
FIG. 4 shows the ill-defined conductance fluctuations induced by ssDNA-CtxA. The top panel corresponds to a continuous 5-minute recording in presence of 5 nM ssDNA-CtxA and shows little pore-forming activity as expected by the low concentration used. The other panels show different zoomed sections, illustrating the noisy and unstable conductance level instead of the usual well-defined conductance levels of native CtxA. All recordings were performed at an applied potential difference of +180 mV.
Figure 5:
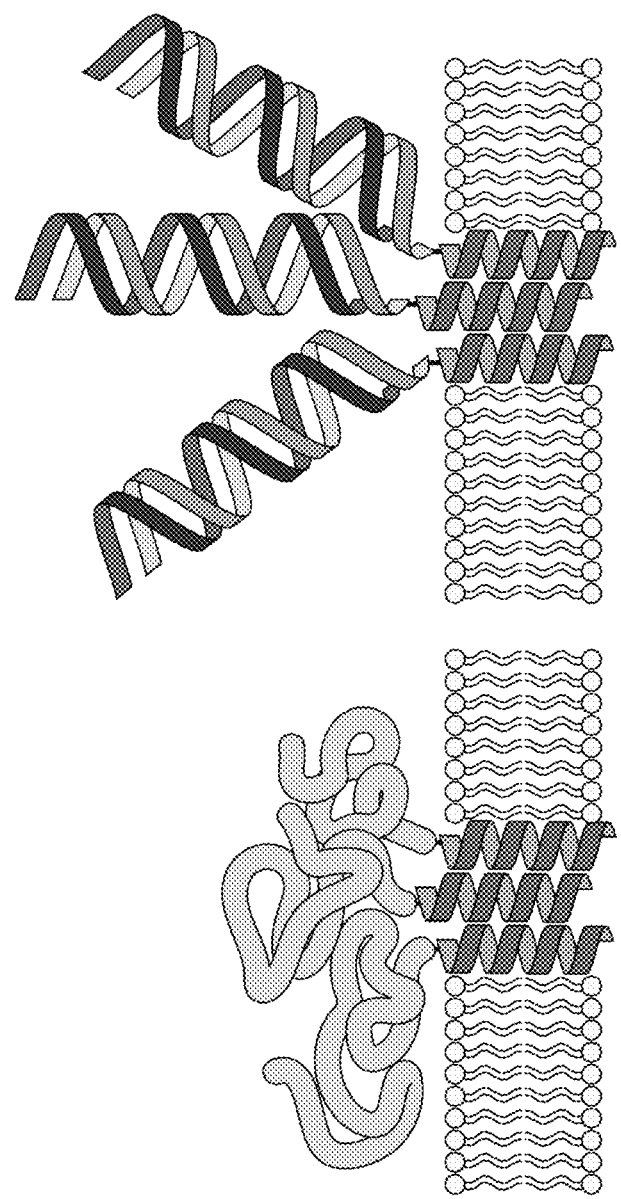
FIG. 5 is a scheme illustrating the DNA-modified CtXA peptide pores. When the DNA part of the peptide is single-stranded, the oligonucleotide can move freely in the solution, potentially covering the pore or being pulled into it. When the DNA is double-stranded, however, the increased rigidity prevents the DNA strands to cover or to be pulled into the pore.

Hydrophobic functionalization for increased pore forming activity. We introduce a cholesterol moiety to increase the affinity of the DNA-assembled peptide pore to the membrane. FIG. 2 compares the activity of different DNA-assembled peptide pores with pores from native CtxA peptides recorded at the same total peptide concentration of 5 nM in single channel recordings with planar lipid bilayer experiments. Typically, native CtxA, CtxA-DNA without any additional strands (ssDNA-CtxA) and CtxA-DNA with the spacer strand (dsDNA-CtxA) exhibit little to no pore formation (FIGS. 2a-c) at these low peptide concentrations. In contrast, CtxA-DNA hybridized to the cholesterol strand (Chol-dsDNA-CtxA) shows frequent p histogram. After addition of a 4-mer template, the relative frequency for observing conductance levels changes dramatically: FIG. 6b shows a strong bias of the distribution towards the conductance of the 4-mer as expected. At the time resolution of our recordings (~20 µs), we observe single-step conductance changes of 330±26 pS, to a level that corresponds to the expected tetrameric pore (FIG. 6b and FIG. 7). The O2 level is only interrupted by very short decreases in conductance. We hypothesized that when a monomer changes from a membrane-spanning conformation to a membrane-laying conformation, it cannot escape the assembly and quickly inserts back into the lipid membrane due to its high local concentration. The conductance rarely increases to levels above the tetrameric pore, further suggesting that this pore comprises four monomers linked together, since free monomers lead to dynamic fluctuations of conductance levels as shown in FIG. 6a.

Dynamic fluctuations of pore diameters however still occurred (FIG. 7, panel 1), with the conductance increasing sequentially from the baseline to O1, O2 and O3. We attribute these results to the presence of free Chol-dsDNA-CtxA hybrids that interact with themselves to form trimers or interact with the templated CtxA-DNA assembly to form off-target pore sizes.

Figure 8:
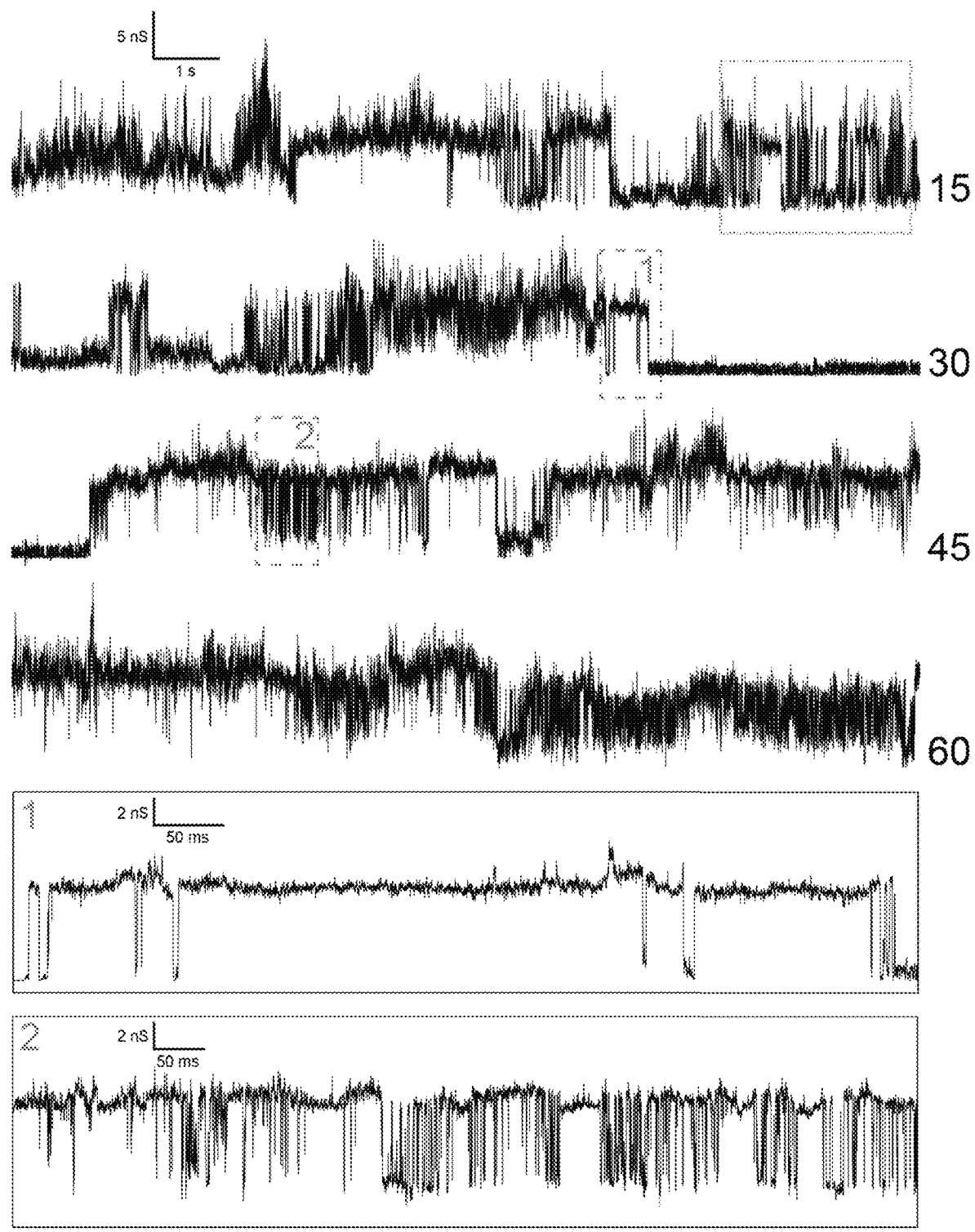
FIG. 8 is a 60-second current trace of an experiment in which the template strand-8-mer was added in a solution containing Chol-dsDNA-CtxA. The zoom of the dotted rectangle is shown in FIG. 6c. The recording was performed at an applied difference of potential of +140 mV and at a Chol-dsDNA-CtxA concentration of 5 nM. In inset 1 and 2 we can see repetitive and distinct increases in conductance from the baseline to the sixth open state, corresponding to incorporation into the bilayer of an octameric pore, with all eight binding sites of the template strand-8-mer occupied.

Further increasing the length of the template to eight or twelve hybridization sites allows the formation of larger pores. We show a two-second recording of such an octameric assembly in FIG. 6c (full 60 s current trace in FIG. 8) and a two-second recording of a dodecameric assembly in FIG. 6d. When using an 8-mer template, we can discern several discrete transitions to conductance values of 8470±700 pS corresponding to insertion in the bilayer of large pore structures. Despite the low concentration (5 nM) of DNA-assembled peptides, we however also observe conductance variations of smaller pores (average conductance value: 1460±270 pS) leading to a non-stable current baseline resulting in discrete conductance steps with a difference of 7010±700 pS. This value is consistent with a pore comprised by eight monomers moving in and out of the bilayer. The histogram of the full 60 s current trace shows this dominant population which corresponds to the 8-mer (O6) as expected by the use of template strand-8-mer. With a template possessing 12 hybridization sites, we observed even larger transitions to conductance values that were closest to the 11- and 12-mer based on the Table 1 values.

Figure 6:
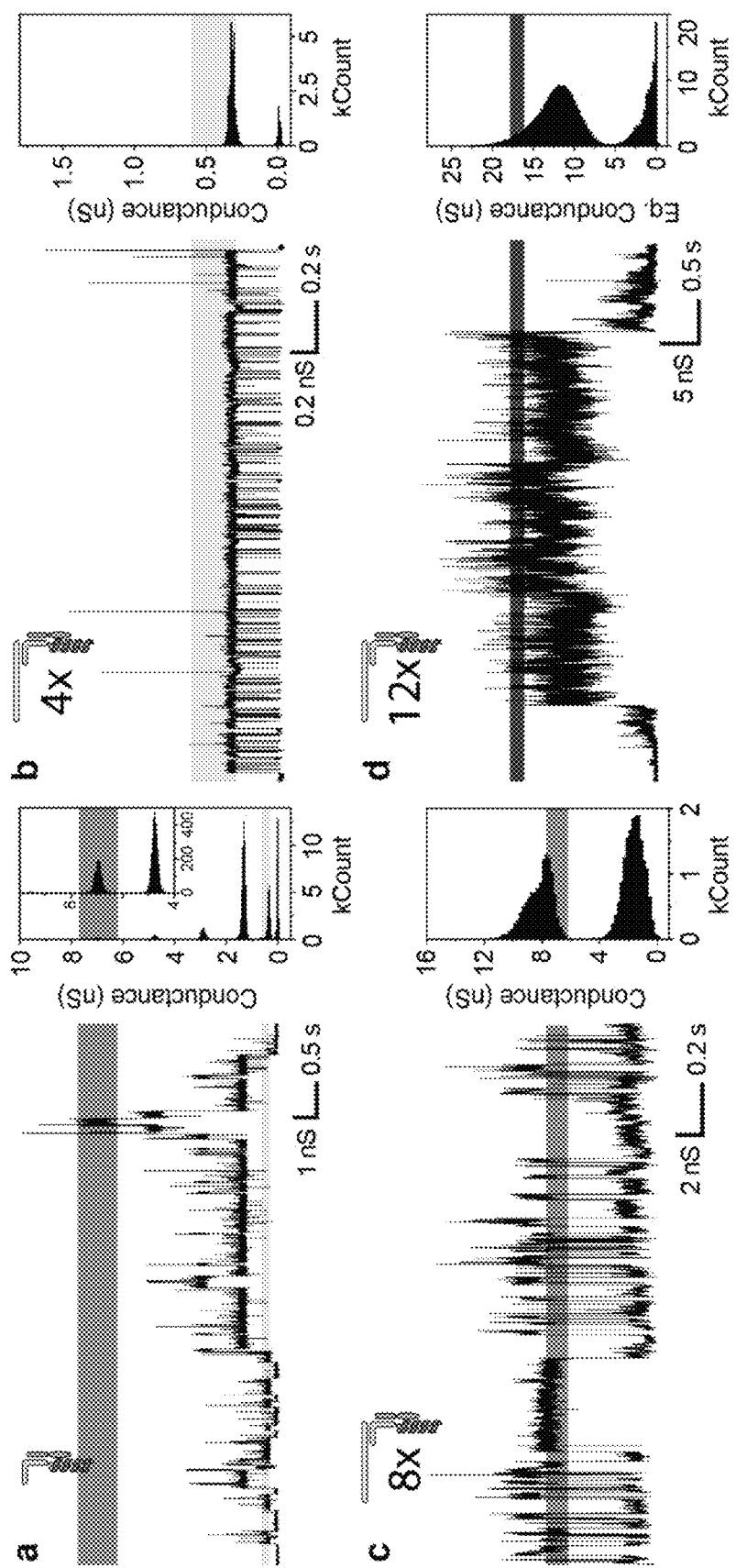
FIG. 6 illustrates templating DNA-modified CtxA peptides leads to preferential pore sizes. Conductance traces versus time are shown, next to the corresponding histograms. (a) Typical CtxA conductance levels observed for Chol-dsDNA-CtxA. (b) In the presence of the 4-mer template, quick fluctuations to the conductance value of a 4-mer pore (O2) occur. Using the 8-mer template (c) and the 12-mer template (d), current steps directly to the conductance value for an 8-mer pore (O6) and even larger fluctuations in the case of the 12-mer, are observed. The colored boxes in the background of the conductance traces of each panel correspond to 4-mer (O2), 8-mer (O6) and 12-mer (O10) conductance levels. The values were calculated by taking the average conductance values from multiple experiments with native CtxA (for O2 and O6) and from an extrapolation of the values of native CtxA conductance open states to find an estimation of the 12-mer conductance. All recordings were carried out with a CtxA-dsDNA-chol concentration of 5 nM (a, b, c) or 20 nM (d) and with applied potential differences of (a and d)+180 mV, (b)+160 mV and (c)+140 mV. Experiments in a, b and c were carried out in 1 M NaCl, 10 mM HEPES in water while experiments in d were carried out in 3 M CsCl, 10 mM HEPES in a 30/70 v/v glycerol/water mixture to increase the stability of the membranes. The conductance values for the latter case have been scaled down to correspond to the conductance values that would have been obtained in 1 M NaCl in water in order to compare efficiently the different experiments.
Figure 7:
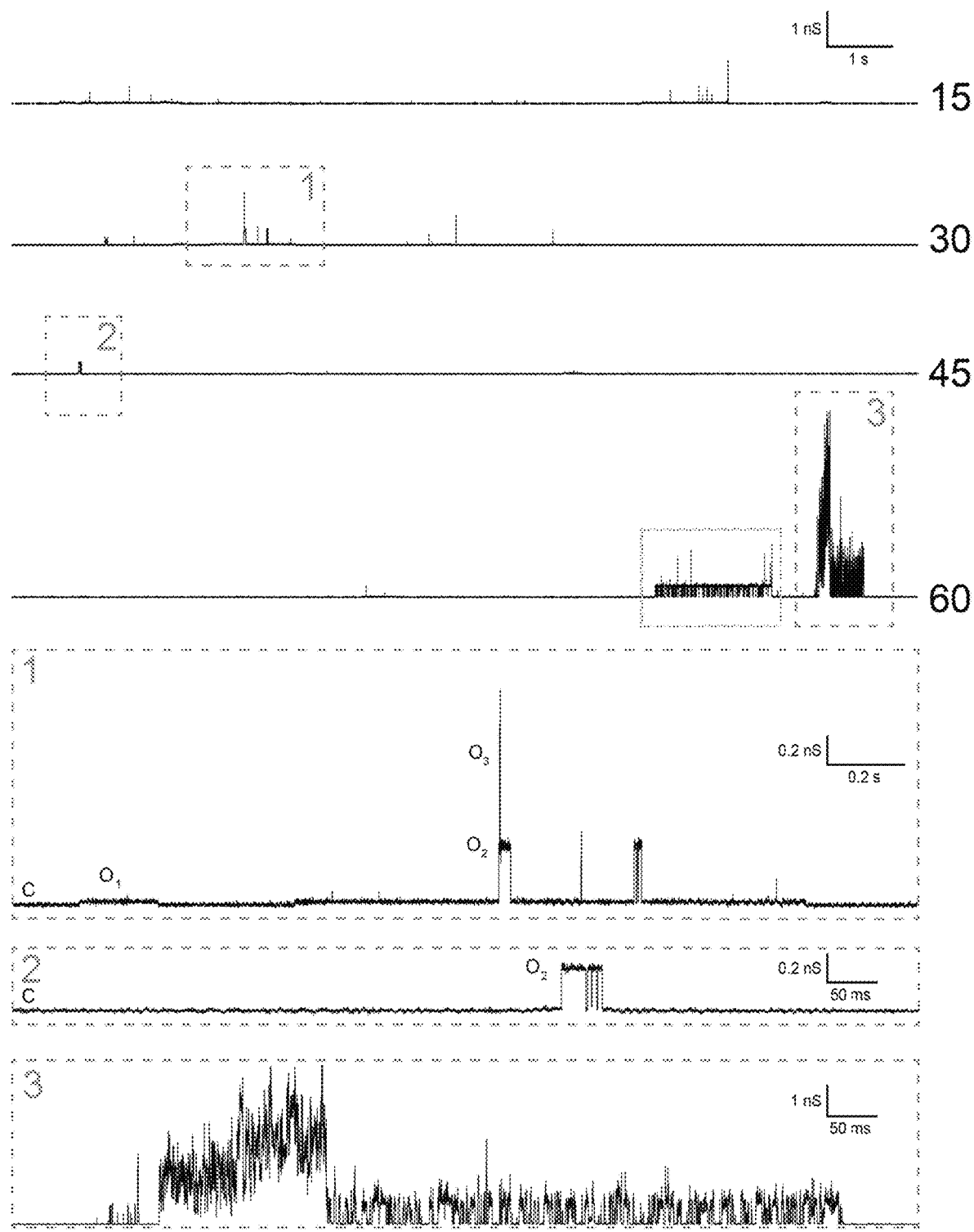
FIG. 7 is a 60-second current trace of an experiment in which the template strand-4-mer was added in a solution containing Chol-dsDNA-CtxA. The zoom of the dotted rectangle is shown in FIG. 6b. The recording was performed at an applied difference of potential of +160 mV and at a Chol-dsDNA-CtxA concentration of 5 nM. In inset 1 regular Chol-dsDNA-CtxAcan be observed while inset 2 shows a distinct increase in conductance from the baseline to the second open state, corresponding to incorporation into the bilayer of a tetrameric pore, with all four binding sites of the template strand-4-mer occupied. Inset 3 shows an increased pore forming activity that does not correspond to the usual CtxA open state conductances and that could not be defined.
Figure 9:
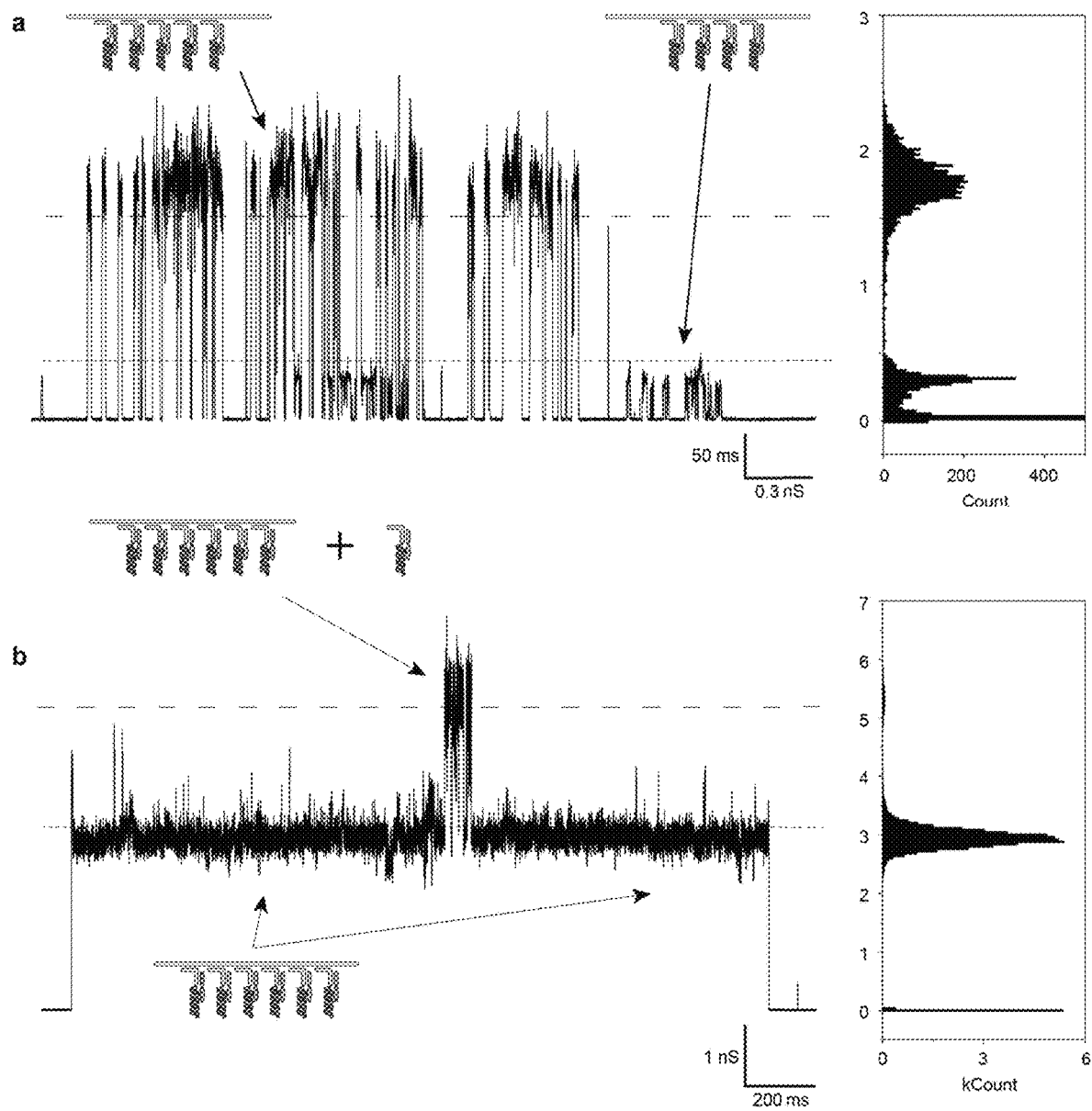
FIG. 9 represents traces of current corresponding to experiments with non-fully occupied template strand-8-mer. (A) Direct insertions in planar lipid bilayers of templated pores comprised by four (dotted line) or five (dashed line) monomers. (B) Direct insertions in planar lipid bilayers of templated pores comprised by six monomers (dotted line). An increase in the current is observed, potentially arising from a seventh monomer joining the templated assembly, resulting in a bigger pore (dashed line). Both traces of current correspond to experiments in which the template strand-8-mer was added in a solution containing Chol-dsDNA-CtxA at a concentration of 0.1 nM. The recordings were performed at an applied potential difference of +200 mV.

While the current traces we show in FIG. 6 display the formation of pores having the expected size, this result was not obtained on each attempt and we often observed fluctuations of the conductance values that might be due to smaller or bigger CtxA open states. We attribute the smaller pores to structures with template strands not fully occupied by the peptide-DNA hybrids. Alternatively, a template strand fully occupied but having one or more monomers not adopting a transmembrane conformation would also lead to smaller-than-expected pores. In FIG. 9, we show two examples of direct insertion into the bilayer of pores comprised of four, five and six monomers when we use the 8-mer template. The occasional observation of conductance increases from one predominant open state to a higher state may correspond to free peptide-DNA monomers joining a templated pore. The current trace we show in FIG. 9b may reflect this possibility. Peptide monomers from different template strands, fully occupied or not, can also aggregate to form larger structures. Two templated pores could for example combine, forming a bigger pore. Using a large excess of DNA-modified monomers compared to the template strand and removal of unbound monomers by purification could potentially reduce the possibility of free peptide-DNA monomers joining templated pores.

Figure 10:
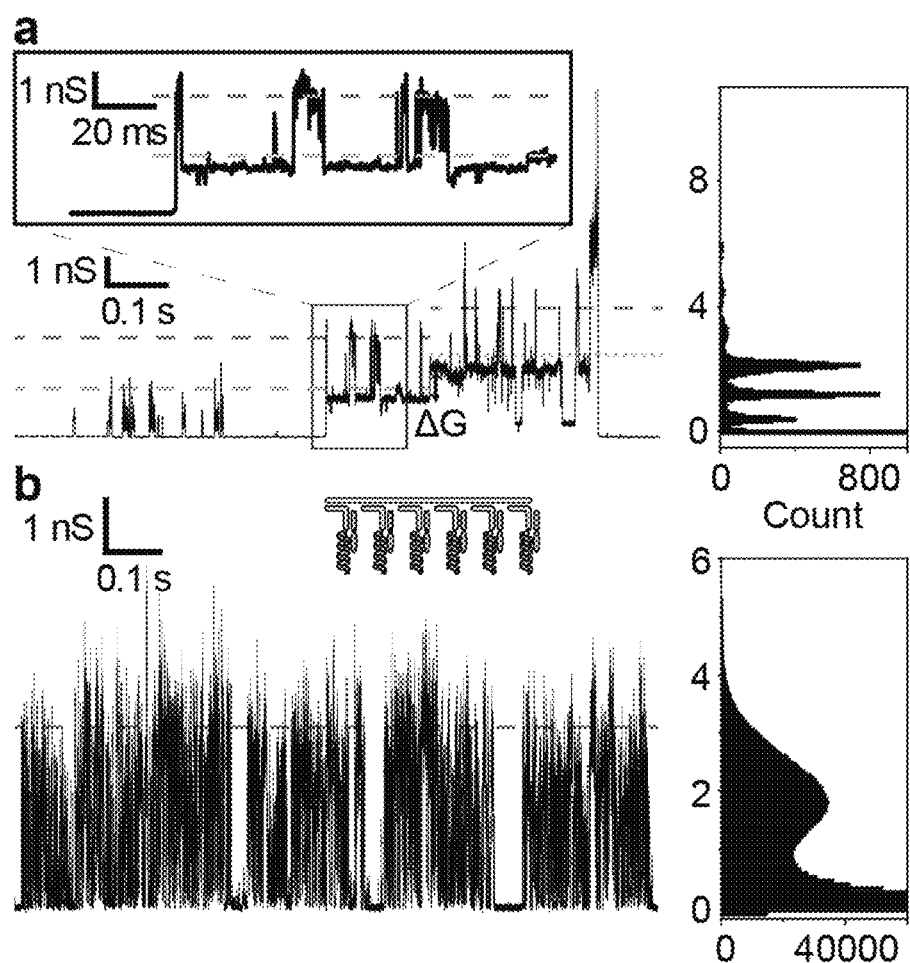
FIG. 10 illustrates the effect of a purification process on the assemblies shown for a hexameric assembly. Conductance traces versus time are shown, next to the corresponding histograms. Conductance variations observed for CtxA-dsDNA-chol in presence of 6-mer template (a) without purification or (b) after purification of the assembly. (a) Without purification different conductance fluctuations can be observed, leading to smaller or bigger pore structures. Inset: zoom showing direct increase in conductance to open state 04 followed most likely by fluctuation of one monomer in and out of the membrane. (b) After purification, the removal of free monomers leads to one main population of pores with a size close to the value expected from the use of a 6-mer template. The recordings were carried out with a CtxA-dsDNA-chol concentration of (a) 1 nM and (b) 4 nM and applied potential differences of +200 mV.

We compare in FIG. 10 two representative experiments displaying pore-forming activity upon addition of Chol-dsDNA-CtxA in presence of 6-mer template, before and after purification of the assemblies. The current trace shown in FIG. 10a is recorded under the same experimental conditions as in FIG. 6, without purification. The initial current transitions seem to correlate with a pentameric activity followed by fluctuations of the conductance between O3 (5-mer) and O4 (6-mer) open states, as shown in the inset of FIG. 10a. As the first increase in conductance was from baseline to O4 conductance value, we attribute these events to a fully templated 6-mer template with one monomer fluctuating in and out of the bilayer. The conductance value later increases by $\Delta G = 1 \pm 0.1$ nS—which might be due to formation of a separate pore—but the fluctuations between 5-mer and 6-mer continue to occur as described by the dotted lines. FIG. 10b displays a 1-second portion of a current trace of the same construct but after purification of the fully assembled 6-mer templates. We now observe one predominant conductance state with a value comprised between the conductance value of a pentamer and the one of a hexamer. While we also observed tetrameric activity, the purification of the templated assemblies circumvents the possibility for free monomers to join the constructs, resulting in more defined structures. The smaller assemblies observed here are most likely induced by monomers that do not adopt the transmembrane conformation.

Figure 11:
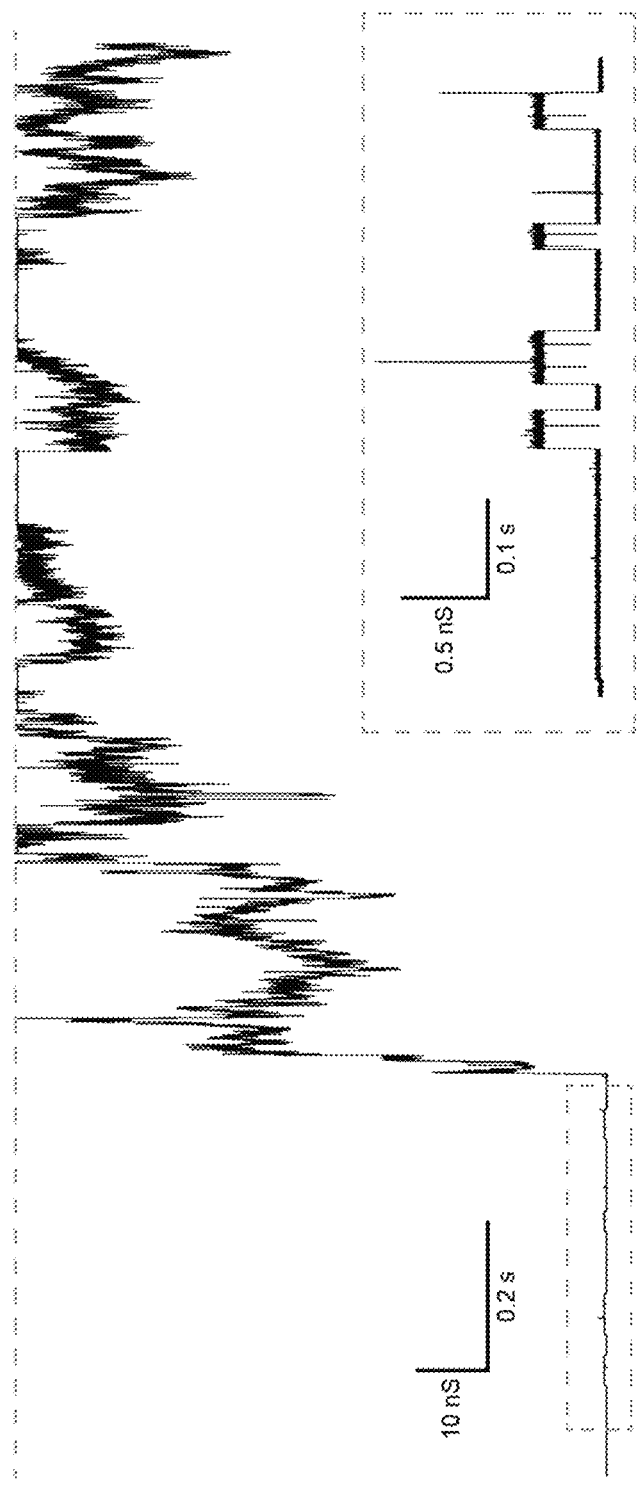
FIG. 11 shows that Addition of 8-mer template in presence of Chol-dsDNA-CtxA leads to high pore formation. This representative trace of current shows intermittent pore formation by Chol-dsDNA-CtxA (added at a concentration of 0.1 nM) followed by an increase in conductance reaching saturation of the amplifier (dashed line, >16 nA). The inset shows a zoom of the beginning of this trace, in which the first three open states of Chol-dsDNA-CtxA can be observed. This recording was performed at an applied potential difference of +180 mV.

In addition to biasing the size of the formed pores towards the desired size, the presence of a template strand also leads to an increased pore formation at lower concentration than without the template. In close to 50% of the experiments, addition of the 8-mer template results in incorporation of many pores in parallel, sometimes exceeding the amplifiers current limit (~16 nA). We present in FIG. 11 an example of increased pore-forming activity in the presence of the 8-mer template in a solution containing Chol-dsDNA-CtxA (0.1 nM). We observe regular Chol-dsDNA-CtxA conductance states with varying levels at the beginning of this current trace, followed by a rapid increase in the conductance exceeding the amplifier limit while the bilayer remains intact. In absence of the template strands, we rarely observe similarly extensive pore-forming activity even at peptide concentrations that are 200-fold higher (20 nM). This high activity clearly demonstrates a strong enhancement of the template and the cholesterol strands on pore formation, especially considering the low peptide-DNA concentration (0.1 nM) used in these experiments.

Formation of pores with defined sizes by DNA templating.

For the assembly of size tuneable pores for resistive pulse sensing, discrete and well-defined DNA objects are required. By employing several partly complementary strands, only flexible constructs with limited complexity can be formed as shown by two recent papers from Henning-Knechtel et al.[7] and Spruijt et al.[6]. In contrast, the DNA origami technique allows the assembly of large, relatively rigid and geometrically well-defined templates with desired shape and atomistic precision. Readily available tools for simple design, production and purification ease the development of these macromolecular constructs. Consisting of one scaffold strand of about 8000 bases and about 200 staples, origami structures can provide a large number of attachment sites for pore formers and other functional groups, for example by affinity moieties, enhancing binding to membranes or moieties to capture target analytes for enhanced detection.

Figure 12:
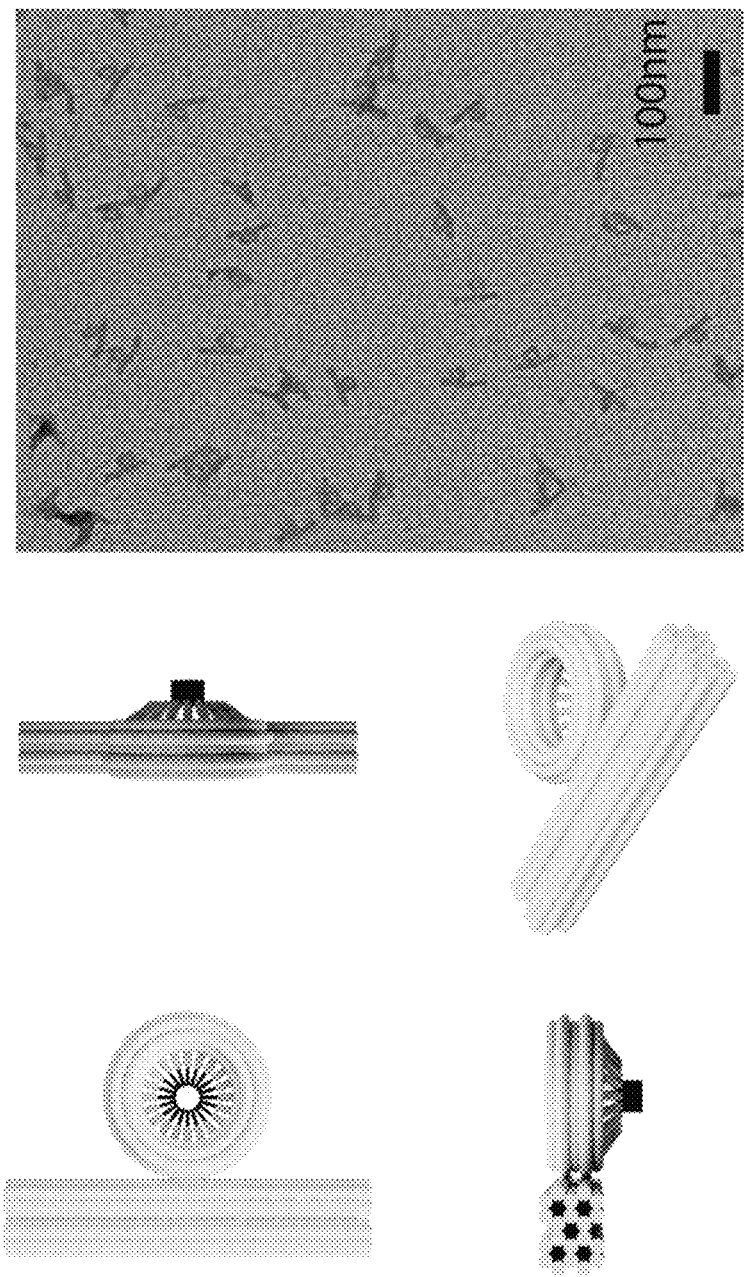
FIG. 12 shows a DNA origami-based template ring. (a) Three-dimensional model of the DNA nanostructure, templating 20 compounds. DNA double helices are depicted as cylinders. Double stranded DNA connections (large radial cylinders) connect the pore forming peptides (thin cylinders in the ring center) which are constituting the final pore. The block structure connected to the ring does not have any function for the pore formation process, but is required to avoid a long single stranded scaffold loop that might interfere with the pore. (b) TEM positive stain images of the DNA origami rings.
Figure 13:
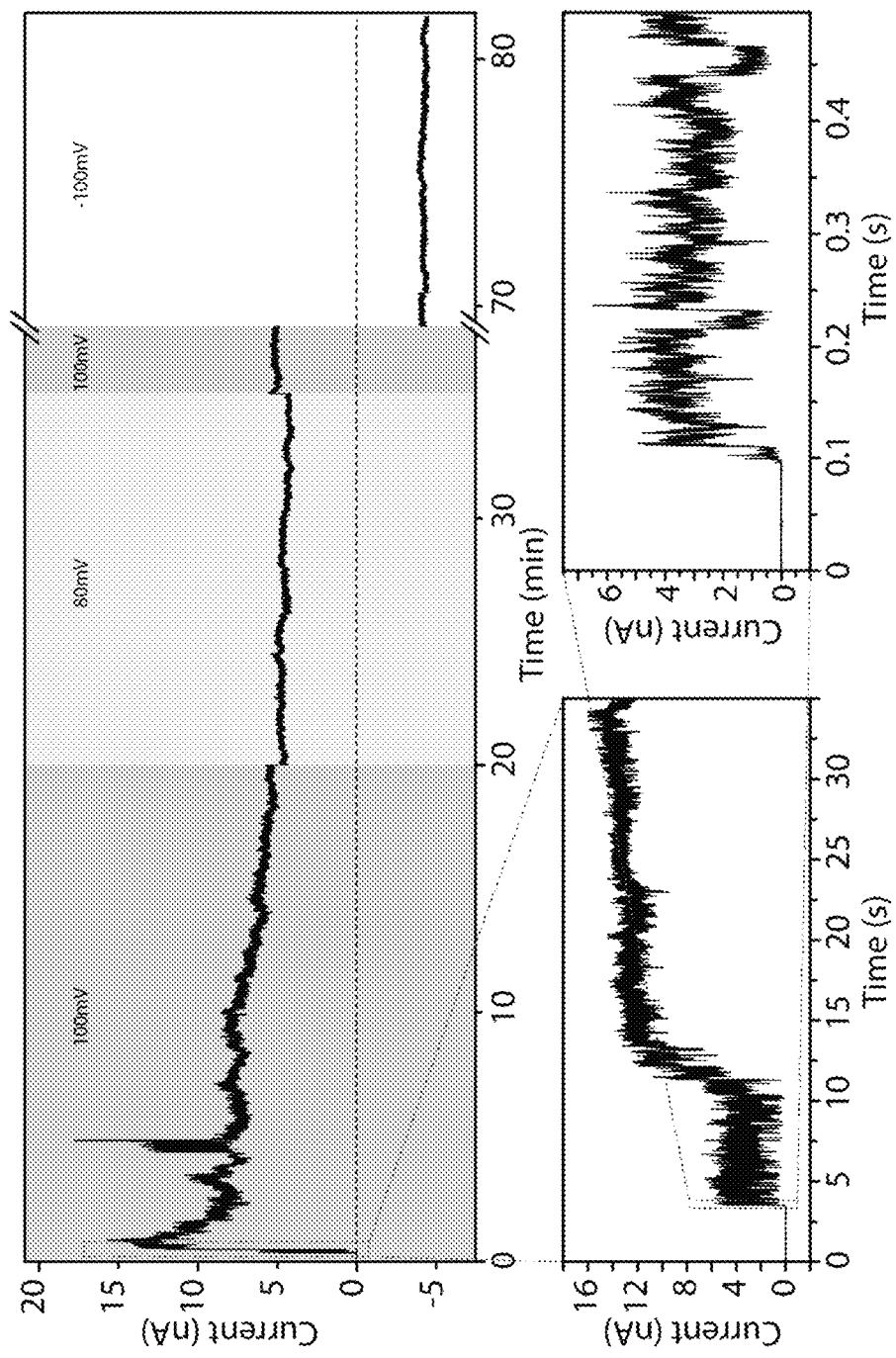
FIG. 13 is a current versus time recording of a DNA origami templated CtxA pore. After insertion of the pore into the lipid membrane, the pore current first fluctuated until reaching a stable value of around 5 nA after about 15 minutes. The pore remained in the bilayer even after reversal of the polarity with the same conductance value. This pore was stable for more than one hour. Two zoomed traces show the insertion process of the pore into the membrane in detail. The current increased with several discrete levels to a maximum of 15 nA. In this experiment, 20 DNA strands each carrying 2 CtxA monomers were attached to the DNA origami ring. A concentration of 20 pM of origami construct was used in that experiment corresponding to a peptide concentration of 0.8 nM.
Figure 14:
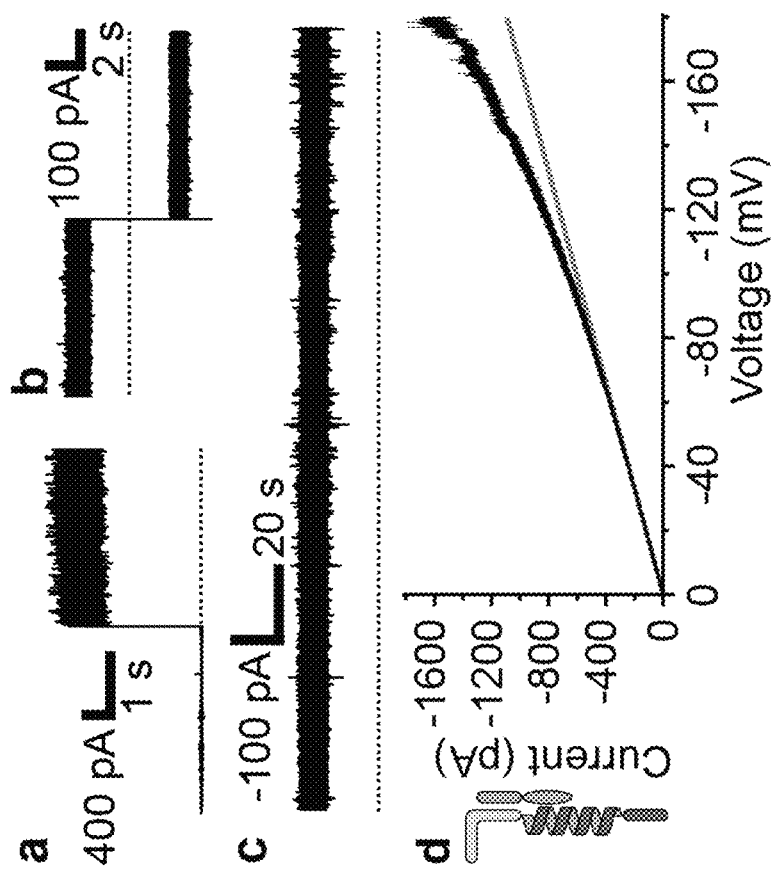
FIG. 14 illustrates a long-lived pore formation by DNA-double modified CtxA peptides. (a) Current-voltage relationship of a long-lived single channel formed by DNA-double modified CtxA monomers. The red curve represents a linear fit resulting in a conductance G=6.4 nS. (b) Apparent single-step insertion of a single pore from DNA-double modified peptides at an applied potential of −180 mV (I=−1512±108 pA). (c) This same pore as in (b) remains in the membrane after reversal of the voltage polarity from −20 mV to +20 mV. (d) A 5-min current trace shows the presence of the pore formed by DNA-double modified CtxA monomers (+20 mV) with a measured current of I=124±7.55 pA.
Figure 15A:
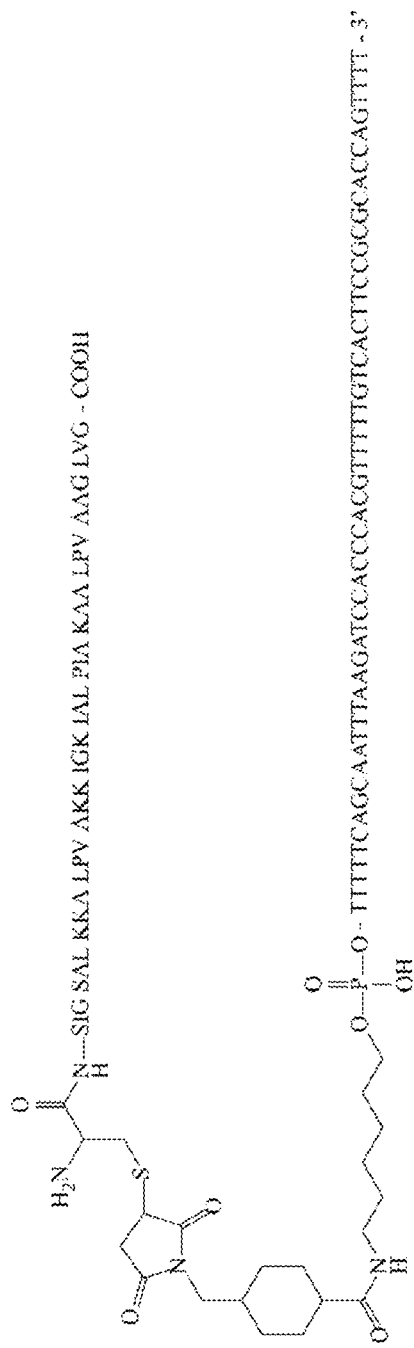
FIGS. 15A-15G display the chemical structures of the different compounds used.
Figure 15B:
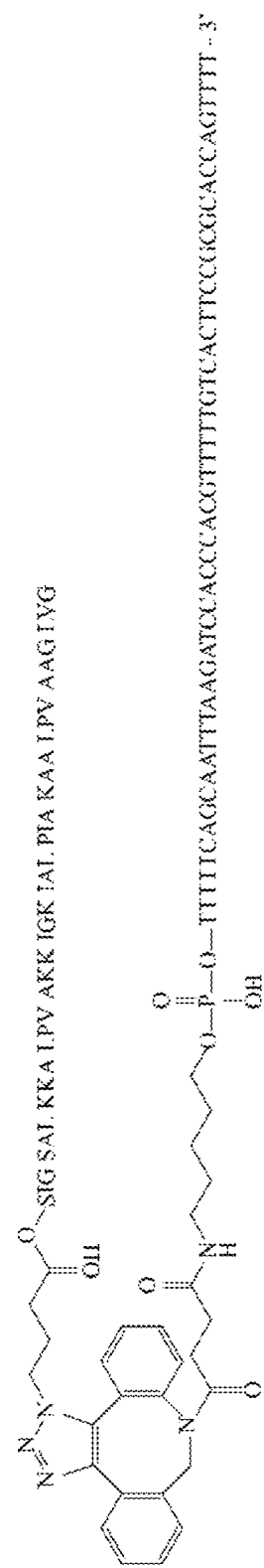
Figure 15C:
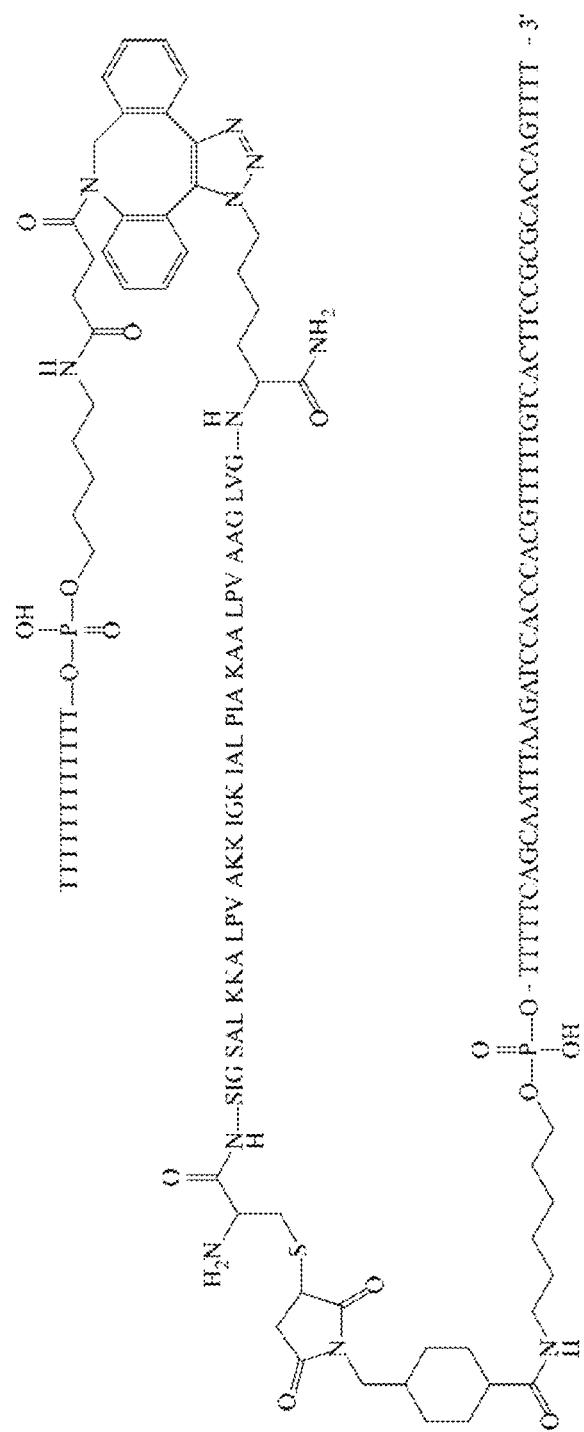
Figure 15D:
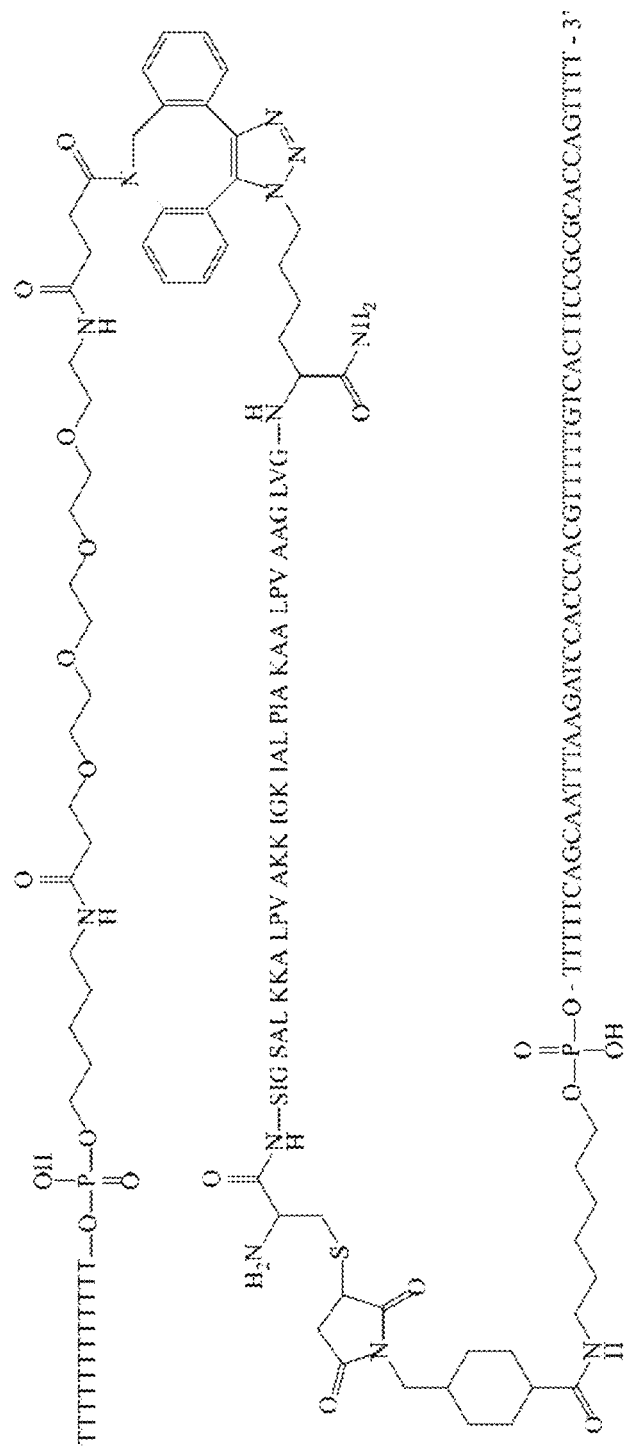
Figure 15E:
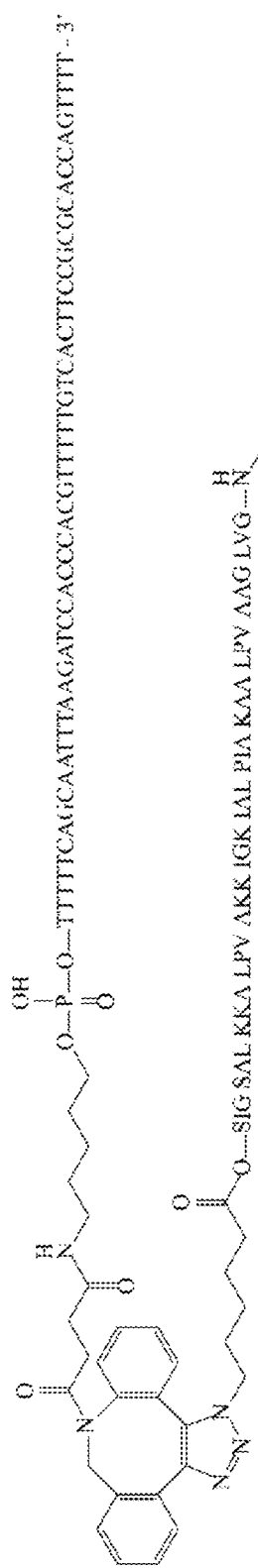
Figure 15E:
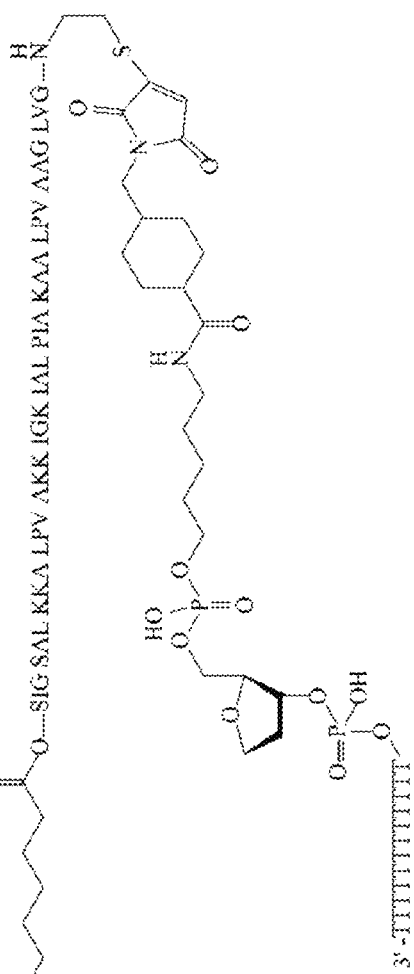
Figure 15F:
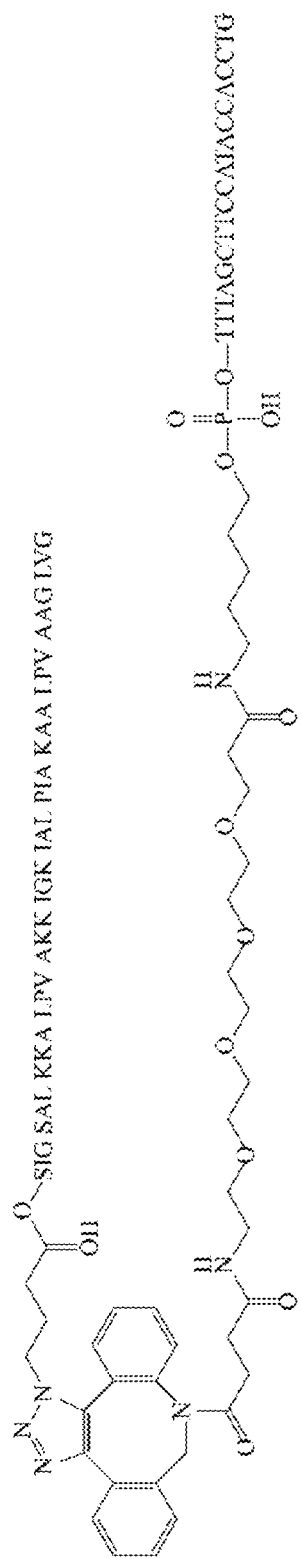
Figure 15G:
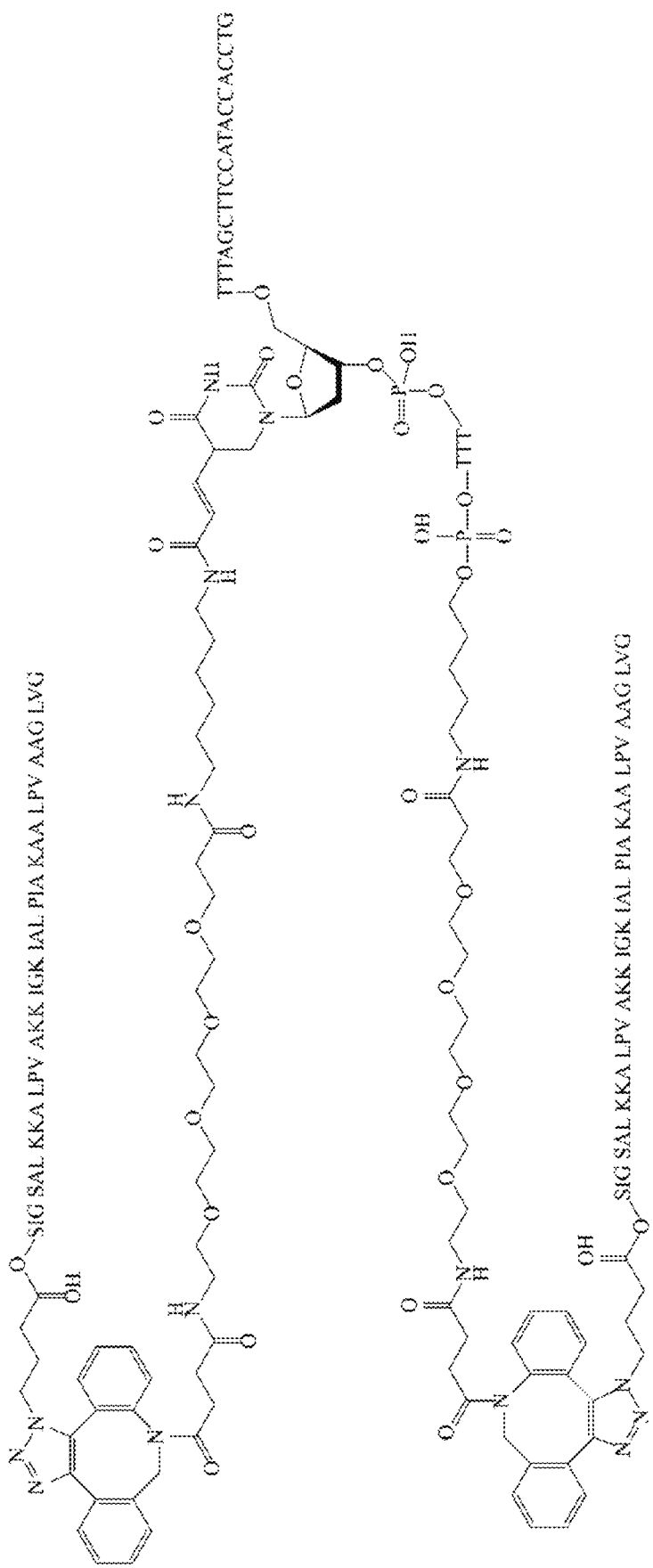
Figure 16:
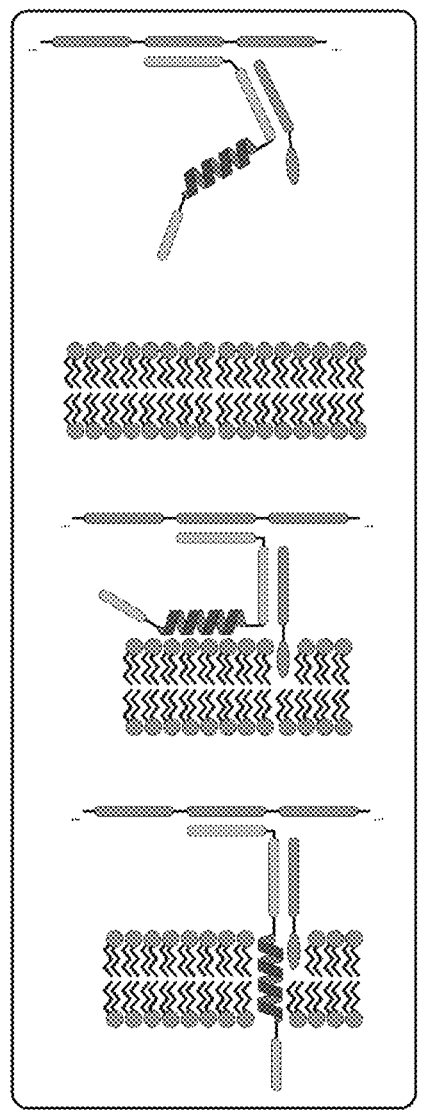
FIG. 16 corresponds to schematic drawings of different macromolecular constructs based on the disclosed compound. Left panel: insertion process of templated Chol-ds-DNA-CtxA-$T_{12}$. The cholesterol strand increases the membrane affinity of the construct by inserting into the bilayer. In the transmembrane conformation, the hydrophilic poly-T segment hinders the peptide to flip back out of the membrane. (1) Templated Chol-ds-DNA-CtxA, (2) templated Chol-ds-DNA-CtxA-T$_{12}$, (3) CtxA-T$_{12}$, (4) templated ss-DNA-CtxA, (5) templated ds-DNA-CtxA, (6) Chol-ds-DNA-CtxA-T$_{12}$ templated from both sides. The strand that links the trans DNA segment to the template on the trans side (i.e. the strand that is shown to have a 90 degree kink) may or may not contain a lipid anchor (such as cholesterol) to stabilize the assembly.
Figure 16:
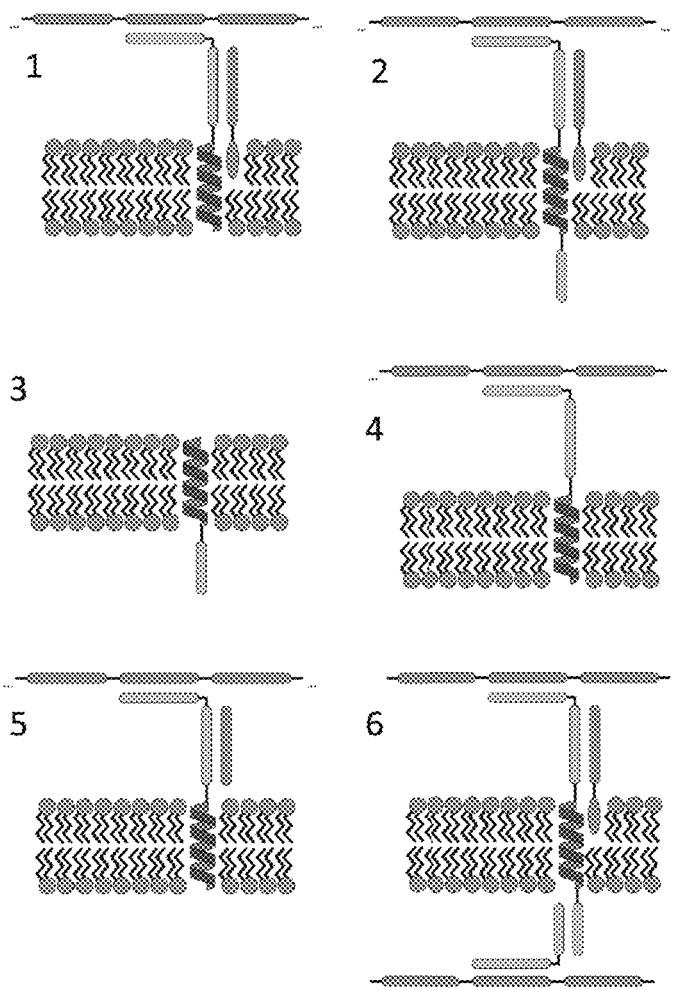
Figure 17:
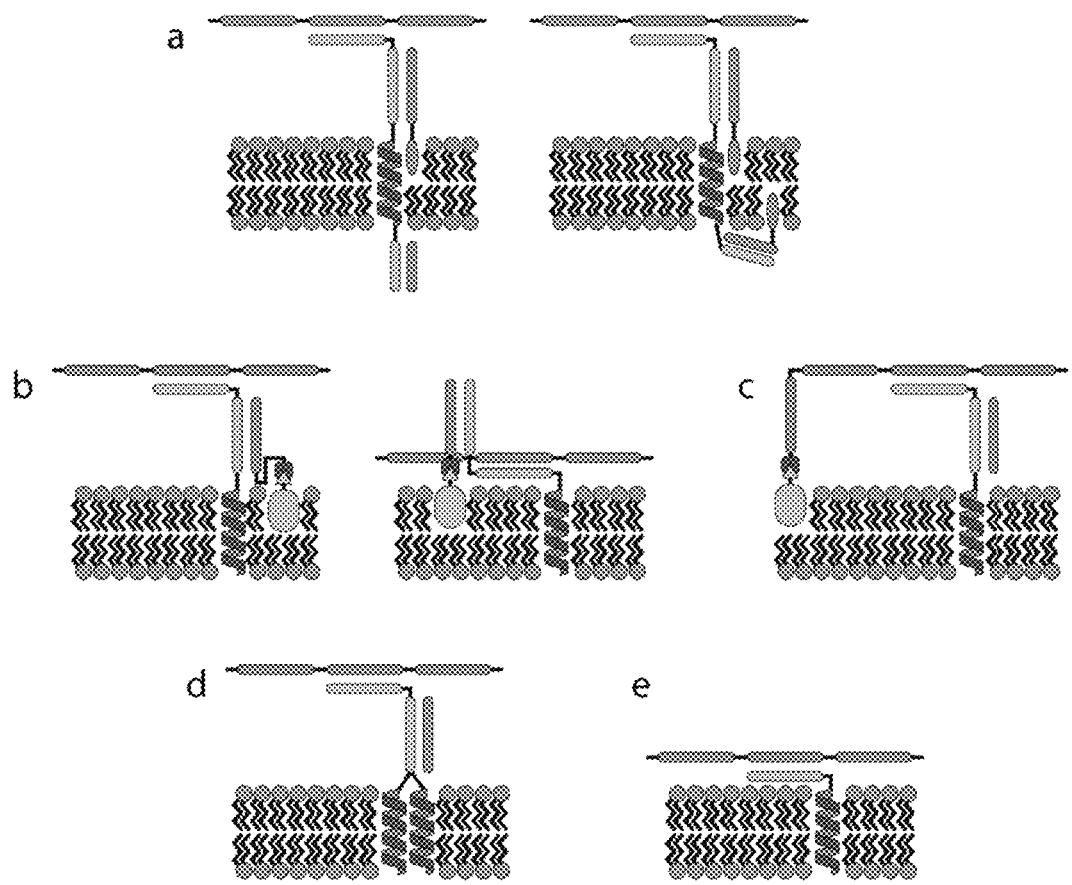
FIG. 17 corresponds to schemes of proposed constructs based on the disclosed compound. (a) Permanently locking of the peptide in a transmembrane conformation by hybridizing a complementary sequence to the second oligonucleotide on the transmembrane terminus. The oligonucleotide to be hybridized can be functionalized with a membrane binder like cholesterol to localize the oligonucleotide on the membrane. (b) Using a receptor-binding moiety as an affinity-increasing agent to target membranes of cells expressing this specific receptor. (c) Affinity moieties can also be attached to the templating strand or structure. We created an embodiment of this principle by attaching cholesterol moieties to the DNA-origami templates. (d) A compound containing multiple pore formers covalently attached to a single DNA strand, allowing creating pores with higher numbers of constituent peptides with the same number of DNA strand. We disclosed this concept already within the DNA-origami based embodiment, where we employed a compound consisting of two CtxA peptides linked to one DNA strand. (e) A compound carrying no linker region but only a template-binding region. Such a simplified compound was used in the DNA-origami based embodiment.
Figure 18:
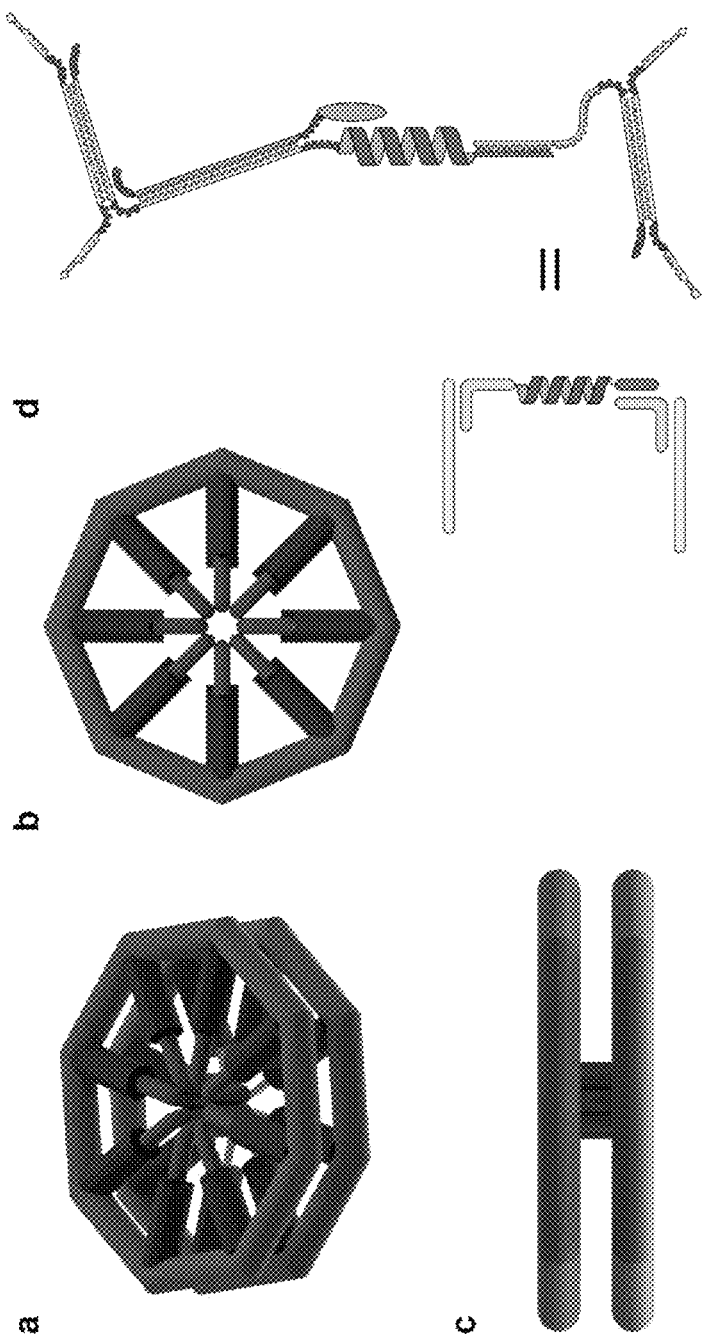
FIG. 18 illustrates another schematic representation of DNA-assembled peptide pores with programmable pore size that are templated from both sides of the membrane (i.e. from cis and from trans) to increase the pore stability. The design can be the same as was used in previous figures or it can be slightly different, with a shorter oligonucleotide covalently linked to the peptide to force the DNA template sterically to lay flat on the membrane instead of extending above the pore. A flat orientation parallel to the membrane plane would circumvent possible transient or permanent blockade of the pore entrance by DNA strands from the template. Such a blockade, if it were to occur, may reduce the probability of analytes to translocate through the pore. (a) Side view, (b) top view and (c) front view of an octameric CtxA pore, templated from both sides (similar double-templating approaches can be pursued with different pore sizes, e.g. tetrameric pores, dodecameric pores and larger). (d) Assembly scheme showing the hybridization of the DNA-peptide pores from both sides.
Figure 19:
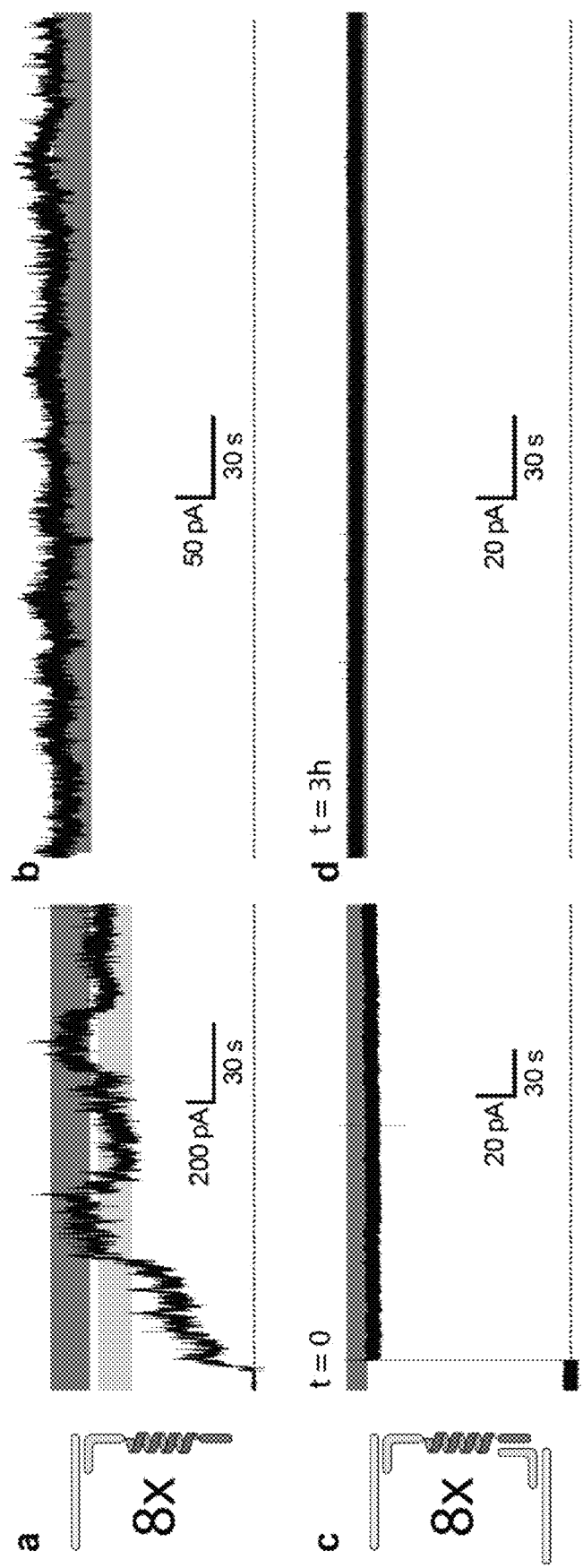
FIG. 19 shows current versus time recordings that illustrate the pore forming behavior of two different peptide-DNA structures. Panels (a) and (b) represent the insertion of CtxA peptides modified with DNA on both termini (dsDNA-CtxA-T$_{12}$) in the presence of the 8-mer template only on the cis side, with an applied potential of +180 mV (a) or +50 mV (b). While the recorded current showed current fluctuations between the 7-mer and the 8-mer levels at the high voltage used (+180 mV), reduction of the voltage to +50 mV resulted in improved stability of this octameric pore at the expected current (i.e. conductance) level of an octameric pore (as indicated by the shaded region). The electrolyte solution consisted in 1 M NaCl, 10 mM HEPES, pH 7.3. Panels (c) and (d) illustrate the improvements made with regard to the stability of such DNA-peptide pores when an 8-mer template is present on both sides of the membrane. Although the applied voltage (+100 mV) is higher than the voltage on panel (b), the resulting pore displays a dramatically improved stability with almost no fluctuations of current during hours of recording. This pore remained open for more than 4 h. The electrolyte solution consisted in 150 mM NaCl, 10 mM HEPES, pH 7.3.
Figure 20:
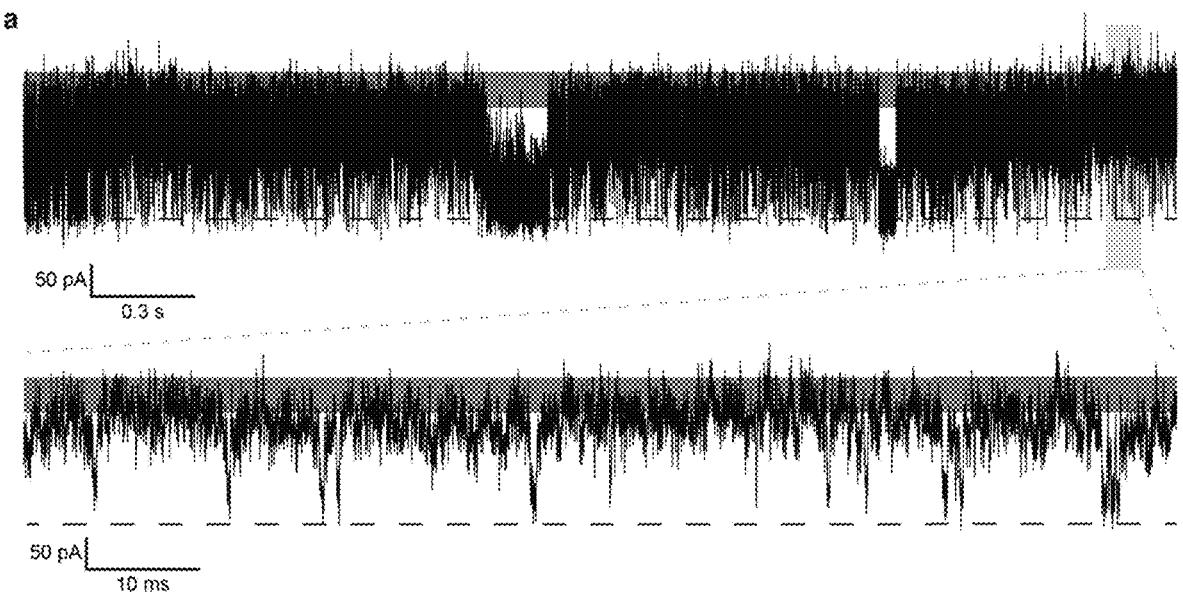
FIG. 20 shows resistive pulses that are consistent with translocation events of macromolecules through DNA peptide pores templated from both sides. The macromolecular analytes consist of a mixture of PEG 4000, PEG 1500, PEG 200 molecules and dextrane sulfate 8000 molecules and were added to a final concentration in the recording chamber of 461 µM, 922 µM, 69 µM and 31 µM respectively. (a) The measured current suggests the presence of an octameric pore incorporated into the lipid membrane. After addition of the macromolecular analyte mixture, multiple current decreases can be observed. The relatively unstable baseline could be due to the template on the trans side not being connected to the pore, leading to unstable pores such as shown is FIGS. 19 a, b. Another explanation could be frequent translocation of small PEG 200 molecules leading to a seemingly unstable baseline. The horizontal dashed line corresponds to 0 pA current. (b) The current value suggests the presence of multiple pores simultaneously in the bilayer. After the last incorporation step and in presence of the mixture of analytes, resistive pulses start to appear, which are consistent with the translocation of macromolecular analytes. This experiment was performed with the same analyte mixture as used in panel a)
Figure 20:
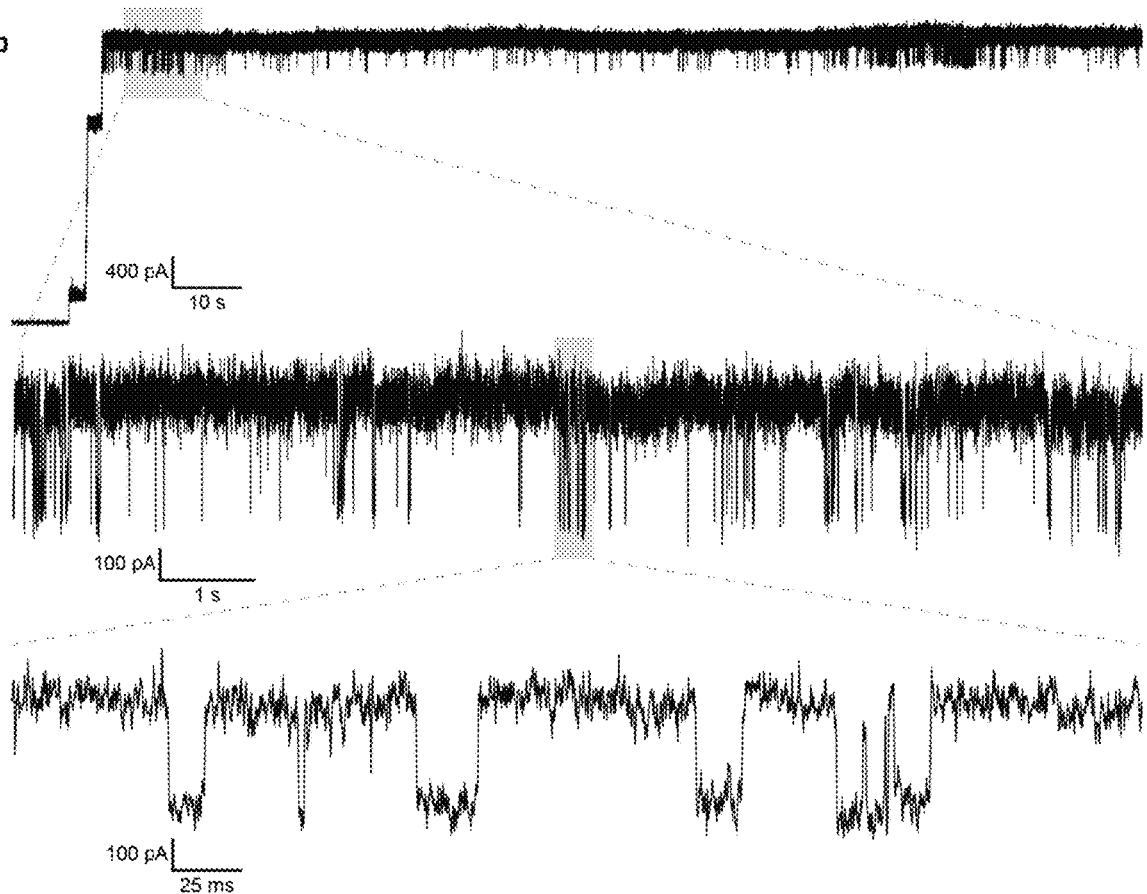

Similar extended nucleic acid structures can also be obtained using other methods like single stranded tile assembly or RNA origami[8,9]. FIG. 12 shows a 3D representation together with a TEM image of such DNA origami-templated CtxA pores. FIG. 13 shows a current trace of a that compound across a planar lipid bilayer. This pore was formed by an origami ring carrying 20 DNA binding sites. Each attached DNA oligonucleotide carries two CtxA monomers attached via PEG linkers, leading to a maximum of 40 templated CtxA peptides. The insertion of the pore occurred with several discrete levels that may be due to the presence in a transmembrane conformation of different number of peptide monomers. The first level, with a current of 0.45±0.25 nA, corresponds to the insertion of 5-8 CtxA monomers is rapidly followed (after around 10 ms) by a second level with a current of 3.6±0.8 nA. This level, corresponding to around 16 CtxA monomers assembled to form a pore, was interrupted by levels of smaller current (1.3±0.4 nA) that we interpreted as a few monomers flipping out of the pore leading to a smaller pore consisting of about 13 monomers. The current kept rising, reaching after 15 seconds a maximum value of 13.8±0.6 nA corresponding to about 30 monomers. 15 seconds later, the pore current started to decrease to finally stabilize at a current value of 5.4±0.1 nA corresponding to about 19 peptide monomers in the pore. This pore was then stable for more than an hour and the voltage could be decreased to 80 mV and even reversed to −100 mV without losing the pore from its inserted state in the membrane. In this experiment, we did not use a cholesterol anchor to increase the affinity of the constructs as they were already active at very low concentrations. In other experiments, with and without cholesterol anchors, we observed long-lived formation of large pores from single-labelled DNA-CtxA conjugates.

We estimated the number of monomers in a pore extrapolated with a polynomial fit to the experiments data from the conductance value of the first six open states of native CtxA.

Hydrophilic modification of the CtxA on the C-terminus results in long-lived open states.

Applications such as sensing require long-lived, stable pores in lipid or polymer membranes. To design CtxA-DNA hybrids that form longer-lasting pores, we added an additional hydrophilic segment consisting of 12 thymine bases to the C-terminal part of the peptide, yielding a CtxA covalently attached on both ends to a DNA strand. We hypothesized that this segment might trap CtxA in a transmembrane conformation once the C-terminal section is transmembrane. This transmembrane DNA sequence allows hybridization of a complementary 12 adenine-bases oligonucleotide that is added on the trans side of the membrane. After hybridization, this double stranded segment is even less likely to flip back to the cis side of the membrane and potentially further stabilizing the pore. Modifying this 12 adenine-based oligonucleotide with a cholesterol moiety could anchor the polyA sequence to the bilayer, increasing the probability for hybridization to the 12 thymine bases of the C-terminal part of the peptide.

FIG. 14*a* shows a current-voltage curve of a single channel inserted in a membrane with a relatively linear behavior. This behavior is unusual for a voltage-gated peptide like CtxA, for which pore formation usually only occurs above a threshold voltage. This result corroborates the assumption that the peptide is stabilized in its transmembrane conformation by the hydrophilic C-terminal modification with $T_{12}$. FIGS. 14*b-d* show insertion of a pore formed by DNA-double modified CtxA monomers into a lipid membrane (b) and its presence in the bilayer at voltages as low as −20 mV (c). We hypothesize that the hydrophilic $T_{12}$ tail hinders the peptide from returning to a conformation that is associated peripherally to the membrane like native CtxA. As FIGS. 14*c-d* show, the nanopore furthermore stayed open within the lipid membrane after reversal of the polarity and remained open for at least 20 minutes without modification of its conductance value (d). In contrast, native CtxA or DNA-assembled CtxA pores without the C-terminal $T_{12}$ modification typically resulted in pores with lifetimes in the range of hundreds of milliseconds about three orders of magnitude shorter.

To explore programmed assembly of CtxA peptides with C-terminal $T_{12}$ modification to long-lived pores of the desired size, we repeated the experiments with an 8-mer template (FIGS. 19*a,b*). While the recorded current showed current fluctuations between the 7-mer and the 8-mer levels at the high voltage used (+180 mV, FIG. 19*a*), reduction of the voltage to +50 mV resulted in improved stability of this octameric pore (FIG. 19*b*). We obtained such long-lasting octamers in 30% of the experiments involving the 8-mer template (N>10); in the remaining experiments, we observed long-lasting pores comprising fewer monomers than expected. Occasionally, we also observed brief, transient fluctuations in conductance, which we again attribute to one or a few peptide monomers leaving and joining the assembly.

Altogether, these results support the hypothesis that the hydrophilic C-terminal modification with $T_{12}$ stabilized the peptides in their transmembrane conformation. Adding a template strand additionally allowed defining the size of the pores. Modifying the transmembrane part of the CtxA peptide, hence provides a strategy for prolonging the open state of pores from pore-forming peptides, which otherwise fluctuate dynamically between conductance levels.

Taking advantage of the $T_{12}$ tail present on the trans side of the membrane, we designed another oligonucleotide sequence possessing two hybridization regions, one to bind to the template and the other one to bind to the $T_{12}$ tail of CtxA. We first prepared and purified structures composed of an 8-mer template and eight of these new oligonucleotide sequences (see FIG. 18*d*, bottom part), referred to as the trans-templating structure. After pore formation by DNA-CtxA-$T_{12}$, the trans-templating structure hybridized to the CtxA peptides through its $T_{12}$ tail (FIG. 18*d*) and led to an improved pore stability (FIGS. 19*c,d*). The pore showed in example in FIGS. 19*c,d* remained in an open state in the membrane for more than four hours.

By modifying the transmembrane part of the CtxA peptide, we provide a pathway for formation of long-lived pores, from pore-forming peptides which otherwise lead to dynamic fluctuations between conductance levels.

After obtaining long-lived and stable pores, we added a mixture of analytes (PEG 4000, PEG 1500, PEG 200 and Dextrane Sulfate 8000, with final concentrations of 461 μM, 922 μM, 69 μM and 31 μM respectively) on the compartments on both sides of the membrane. We show in FIG. 20 current traces from two different experiments after addition of the analytes to octameric pores formed by CtxA peptides modified with DNA on both ends. FIG. 20*a* shows multiple decreases in current from a baseline corresponding to an open octameric pore. FIG. 20*b* also displays several current decreases that could correspond to translocations of molecules. The current first increased in multiple steps which we attributed to the insertion of multiple pores in the membrane. The potential translocations, however, only started to appear after the last current step which would suggest that the analytes could only pass through this pore. Another hypothesis is that the pore grew in steps and the translocations appeared when the pore was big enough to allow the molecules to pass through the pore.

Assembling CtxA pores with the 4-mer, 6-mer, 8-mer or 12-mer templates prevented the replication of cancer cells at lower concentrations than native CtxA.

DNA templating of CtxA pores could serve to enhance toxicity of pores in applications of targeted cell killing. Biologically, the antimicrobial peptide CtxA is produced by the Medfly Ceratitis capitata, in order to protect its eggs[10]. As cytotoxicity of pore-forming antimicrobial peptides correlates with pore size and pep-tide concentration[11], we hypothesized that templating CtxA would kill pathogen or cancer cells at lower concentrations than native CtxA, because templating results in a high local concentration and in larger pores than non-templated CtxA[11].

Figure 21:
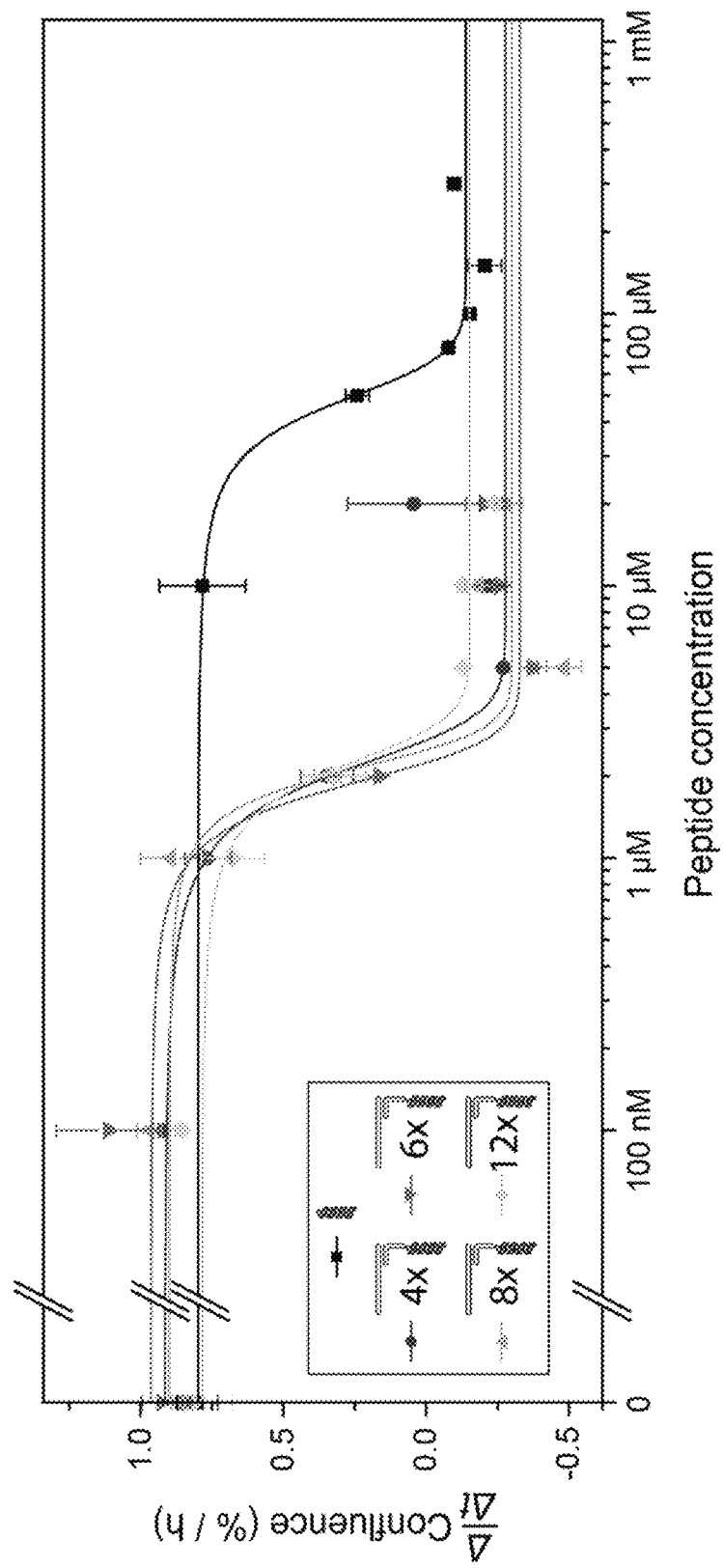
FIG. 21 shows the influence of the DNA templates on the cytotoxic activity of ssDNA-CtxA peptides on A549 cells. The plots show the change in confluence of A549 cells over time as a function of the concentration of templated and non-templated CtxA peptides. For native CtxA peptides, concentrations of 50 to 100 µM were necessary to reduce cell viability. In the case of the DNA-templated pores (tetramers, hexamers, octamers and dodecamers), less than 2 to 5 µM of total CtxA concentration was sufficient to completely stop the replication of the same cells and hence a more than 20-fold lower concentration compared to native CtxA peptides.

To investigate the cytotoxic activity of templated DNA-peptides, we monitored the growth of the epithelial lung cancer cell line A549 upon addition of 4-mer, 6-mer, 8-mer or 12-mer templated CtxA peptides compared to adding native CtxA as control. As a metric for cell viability, we determined the change in confluence over time for each peptide concentration. FIG. 21 shows that 50 to 100 µM of native CtXA were necessary to reduce cell viability. In the case of the DNA-templated pores of CtxA, less than 5 µM of total CtxA concentration was sufficient to completely stop the replication of the same cells. Similar toxicity required 100 µM of native CtxA, and hence a more than 20-fold higher concentration compared to templated CtxA peptides.

CONCLUSION

A modular assembly platform based on the 36-amino acid pore-forming peptide CtxA using DNA nanotechnology is disclosed. Covalently linking the peptide to a single-stranded DNA oligonucleotide also allows simple functionalization of the peptide-DNA hybrid with a cholesterol-bearing DNA strand, drastically increasing the peptide's affinity to the membrane as well as its propensity to form well-defined conductance states. Employing DNA template strands with a defined number of binding sites for the DNA-modified peptide monomers preferentially leads to pores of predefined size. We demonstrate tetrameric, hexameric, octameric and dodecameric assemblies with estimated inner diameters ranging from approximately 0.5 to 3.9 nm based on the conductance values. While these templated assemblies still formed short-lived pores like native CtxA, the addition of a hydrophilic DNA domain to the transmembrane side of the CtxA peptide traps the peptide monomers in a membrane-spanning conformation. This modification results in long-lived pore formation, which can last as long as 30 minutes at one stable and constant conductance level. Alternatively, rigid DNA origami structures allowed templating more monomers (up to 40 in this presented attempt) and thus forming larger pores. These origami pores were also stable for longer times than native CtxA, reaching open pore duration of more than 80 minutes.

DNA-mediated assembly of pore-forming peptides provides several distinct advantages compared to pores traditionally used in nanopore sensing: (i) sub-nanometer fine-tuning of the pore diameter with single monomer increments by using templating structures, (ii) the presence of a loose and open DNA-based frame, without additional resistance caused by a vestibule, (iii) sequence-specific orthogonal hybridization chemistry for targeting defined positions in the structure, (iv) straight-forward design with three different species, (v) potential to open new pathways for adding specific functions such as receptors, antibodies or aptamers, and (vi), possibility to kill cancer cells at more than 20-fold lower total peptide concentrations compared to non-templated CtxA peptides. This result, in principle, makes it possible to use the addition of a DNA template to trigger pore formation in situ by using a DNA-CtxA peptide concentration that is too low for killing before addition of the template. Future extensions of this work may target specific cell types[12], pathogens or analytes by hybridizing ssDNA-tagged ligands, antibodies or aptamers to the construct.

In summary, DNA engineering of CtxA monomers with a straight-forward design makes it possible to form long-lasting, well-defined pores with constant single-channel conductance that can potentially be useful for sensing, drug delivery and pathogen cell killing applications.

Methods

DNA-Modified Peptides Preparation

The compounds are commercially synthesized from a CtxA derivative bearing the DNA oligonucleotide (ssDNA-CtxA) or reacted in-house. Therefore, an CtxA containing an azide group (Azide-CtxA) on its N-terminus reacts overnight via click-chemistry to dibenzocyclooctyne (DBCO)-containing oligonucleotide of the desired sequence. CtxA with a hydrophilic tail is formed from ssDNA-CtxA modified with an azide group on its C-terminus (ssDNA-CtxA-Azide) or with an Azide-CtxA having a thiol group on its C-terminus (Azide-CtxA-Thiol). ssDNA-CtxA-Azide and Azide-CtxA-Thiol then react with an excess 12T-DBCO or 12T-maleimide to form ssDNA-CtxA-12T. High Pressure Liquid Chromatography (HPLC) is then used to remove the excess, unreacted species, ssDNA-CtxA-12T monomers are added in large excess to a solution containing the template strand and HPLC is used to collect the full assemblies and remove the excess ssDNA-CtxA-12T monomers. We confirmed the successful conjugations by HPLC peptide mapping, SEC or SAX. The chemicals were solubilized either in pure water or in TE buffer. FIG. 15 shows the chemical structure of the linkers used for the different compounds we used.

Lipids Preparation/Planar Lipid Bilayer Formation

The lipid composition for the bilayers consisted of POPC, DOPE and POPS with a 7:3:1 (w/w) ratio (PC/PE/PS) or for the origami structures in diphytanoyl phosphatidylcholine (DiPhyPC). We dissolved the resulting lipid mixture in pentane (total lipid concentration: 10 mg/mL). The buffered electrolyte solution consisted of 1M NaCl, 10 mM HEPES, pH 7.4 or 3M CsCl, 10 mM HEPES, pH 7.4 in 30% glycerol.

We designed Teflon chambers with one big compartment (containing a maximum volume of 1.5 mL) and one small compartment (containing a maximum volume of 200 µL). We pretreated Teflon films (Eastern Scientific LLC, Rockville, MD) with apertures of 50 µm by pipetting 1 µL of pre-treatment solution—hexadecane in hexane 2.5% (v/v)—onto both sides of the aperture of the Teflon film. We then mounted the Teflon film in a Teflon chamber using high-vacuum grease (Dow Corning Corporation), separating the two compartments of the Teflon chamber. The only connection between the compartments was the aperture in the Teflon film over which we formed virtually solvent-free planar lipid bilayers using the technique described by Montal and Mueller[10]. Briefly, we added electrolyte solution to both compartments (1.2 mL in the bigger compartment and 160 µL for the smaller one) and spread 1-2 µL of lipid solution onto the surface of the buffered electrolyte solution. After the solvent evaporated, a lipid monolayer (Langmuir film) formed at the air-water interface. We raised and lowered the electrolyte solution until we measured a baseline current (−3 pA<I<3 pA) indicating that a bilayer had formed. We then thinned the membrane by lowering and raising the electrolyte solution in one compartment, until we measured a capacitance of 60±10 pF. To monitor capacitance, we applied a triangular voltage and the capacitance was either calculated by the amplifier or determined visually using the manual capacitance compensation of the amplifier. Prior to adding the peptide, we checked the stability of the bilayer (absence of leak currents, expected noise level) by applying transmembrane voltages of up to 200 mV for 5 min at both polarities. We used one of two different amplifiers, an EPC7 (HEKA Instruments Inc., Holliston, MA, USA) or a BC-535 (Warner Instruments Hamden, CT, USA)) and connected both compartments to the amplifier through two Ag/AgCl pellet electrodes (Warner Instruments Hamden, CT, USA). We placed the Teflon chambers inside Faraday cages, on BM4 vibration isolation platforms (Minus K® Technology, Inc., Inglewood, CA, USA). We carried out all experiments at room temperature (22±1° C.) and tested all setups with different model cells to confirm proper functionality of the amplifiers and function generators. We sampled currents at 50 kHz and low-pass 10 kHz. We analysed data using OriginLab (OriginLab Corporation, Northampton, MA, USA) and pClamp (Molecular Devices, Sunnyvale, CA, USA) software.

Flexible Template Experiments

We performed the experiments with the peptide-DNA hybrid in two different ways: (i) we added all components sequentially—ssDNA-CtxA first, then the template strands, one after the other—or (ii) we mixed the ssDNA-CtxA with the spacer strand (with or without cholesterol) and the template strand in a DNA LoBind tube (Eppendorf Tubes, Hamburg, Germany) and let them react overnight at room temperature (pre-incubation experiments). We also performed the pre-incubation experiments with and without HPLC-SEC purification. In the case of unpurified assemblies, we added the DNA-modified peptides and the spacer strand stoichiometrically and then added the n-mer template (with n equal to 4, 6 or 8) at a ratio of 1 mole for n moles of DNA-modified peptide. When purifying the assemblies, we added the peptide-DNA monomers in excess compared to the template strand (at least 5 n moles of peptide for 1 mol of n-mer template) and removed the excess monomers using HPLC-SEC purification (Agilent SEC 3 column, 300 mm, 300 nm pore size, 4.6 mm internal diameter). We then stored the collected assemblies at +4° C. for later use and add the spacer strand in excess prior to the experiment. When a cholesterol moiety is bound to the spacer strand, we heat the strand for 5 minutes at +60° C. to avoid aggregation of the cholesterol moieties. For the experiments with sequential addition, we added the various components at concentrations in the nanomolar range, while for pre-incubation experiments, we added all the components in micromolar concentrations and later diluted the samples prior to adding them to the buffered electrolyte solution.

Origami Structure Assembly Protocol

To fold the origami structures, we mixed 50 nM scaffold with a 4-fold molar excess of staple strands in a 20 mM MgCl$_2$ solution containing TE buffer. We heated the structures to 90° C. and cooled them down slowly from 57° C. to 49° C. within 18 hours. Subsequently, we removed the excess staples from the folded structure by PEG precipitation as described elsewhere[11]. Within the PEG purification, we changed the buffer to TE containing 1M NaCl.

For attachment of CtxA to the origami constructs, we added the peptide-oligonucleotide conjugates to the structures with a five times molar excess and incubated for at least one hour at room temperature. We finally removed unbound peptides and peptide-DNA conjugates by HPLC size exclusion chromatography (Agilent SEC 3 column, 300 mm, 300 nm pore size, 4.6 mm internal diameter).

We heated the cholesterol oligonucleotides to 60° C. for 5 minutes before attachment to the origami structures. When required, we added the cholesterol strands with a final concentration of 1 µM to the origami constructs directly before use, without further purification.

Cell Culture Experiments.

We grew lung epithelial A549 cells in RPMI 1640 medium containing 25 mM HEPES, 1% L-glutamine, 10% fetal bovine serum and added 1% penicillin-streptomycin for prevention of bacterial contamination of cell cultures. We seeded the cells in 96-well plates (TPP, Trasadingen, Switzerland) with 10'000 cells per well, in a total volume of 50 uL per well. We placed the plates in the IncuCyte Zoom imaging system (Essen Bioscience, Ann Arbor, MI, USA) placed inside of an incubator set to 37° C. and 5% CO2 and monitored the growth of the cell by monitoring the change in confluence over time. We seeded the cells and left them to adhere and replicate for 20 h before adding the templated CtxA-DNA assemblies or native CtxA as control. We then measured the cell confluence every 2 h. To estimate the effect of the different peptide assemblies on the change in confluence over time, we fitted the observed confluence levels after peptide addition linearly.

DNA and Amino Acid Sequences

FIG. 15 furthermore illustrates the linker chemistry of the compound.

CtxA's amino acid sequence is shown in SEQ ID N01.

The nucleotide sequences of the oligonucleotides used with the flexible templates and shown in SEQ ID NO2 to 4.

Sequences are provided from 5' to 3' as generated from the design software cadnano.

The sequences of the block component staples are shown in SEQ ID NO5 to 148. The sequences of the unmodified ring staples are shown in SEQ ID NO149 to 165. The cholesterol strand sequence and the sequence of the strand used to attach the CtxA peptides are shown in SEQ ID NO166 and 167. The sequences of the peptide attachment sites are shown in SEQ ID NO168 to 188. The sequences of the cholesterol attachment sites are shown in SEQ ID NO189 to 196. The scaffold sequence is shown in SEQ ID NO197.

For the avoidance of doubt, the compositions of the present invention encompass all possible combinations of the components, including various ranges of said components, disclosed herein. It is further noted that the term "comprising" does not exclude the presence of other elements. However, it is to also be understood that a description of a product or composition comprising certain components also discloses a product consisting of said components. Similarly, it is also to be understood that a description of a process comprising certain steps also discloses a process consisting of the steps.

In accordance with the patent statutes, the best mode and preferred embodiment have been set forth; the scope of the invention is not limited thereto, but rather by the scope of the attached claims.

REFERENCES

1 Langecker, M. et al. Synthetic lipid membrane channels formed by designed DNA nanostructures. *Science* 338, 932-936, doi:10.1126/science.1225624 (2012).

2 Krishnan, S. et al. Molecular transport through large-diameter DNA nanopores. *Nat Commun* 7, 12787, doi: 10.1038/ncomms12787 (2016).
3 Burns, J. R., Stulz, E. & Howorka, S. Self-assembled DNA nanopores that span lipid bilayers. *Nano Lett* 13, 2351-2356, doi:10.1021/nl304147f (2013).
4 Burns, J. R. et al. Lipid-bilayer-spanning DNA nanopores with a bifunctional porphyrin anchor. *Angewandte Chemie* (International ed. in English) 52, 12069-12072, doi: 10.100²/anie.201305765 (2013).
5 Burns, J. R., Seifert, A., Fertig, N. & Howorka, S. A biomimetic DNA-based channel for the ligand-controlled transport of charged molecular cargo across a biological membrane. *Nature Nanotechnology* 11, 152, doi:10.1038/nnano.2015.279 https://www.nature.com/articles/nnano.2015.279#supplementary-information (2016).
6 Spruijt, E., Tusk, S. E. & Bayley, H. DNA scaffolds support stable and uniform peptide nanopores. *Nature Nanotechnology*, doi:10.1038/s41565-018-0139-6 (2018).
7 Henning-Knechtel, A., Knechtel, J. & Magzoub, M. DNA-assisted oligomerization of pore-forming toxin monomers into precisely-controlled protein channels. *Nucleic Acids Research*, gkx990-gkx990, doi:10.1093/nar/gkx990 (2017).
8 Ke, Y., Ong, L. L., Shih, W. M. & Yin, P. Three-Dimensional Structures Self-Assembled from DNA Bricks. *Science* 338, 1177-1183, doi:10.1126/science.1227268 (2012).
9 Wei, B., Dai, M. & Yin, P. Complex shapes self-assembled from single-stranded DNA tiles. *Nature* 485, 623, doi: 10.1038/nature11075 https://wvvw.nature.com/articles/nature11075#supplementary-information (2012).
10 Marchini, D., Marri, L., Rosetto, M., Manetti, A. G. & Dallai, R. Presence of Antibacterial Peptides on the Laid Egg Chorion of the Medfly *Ceratitis capitata*. *Biochemical and biophysical research communications* 240, 657-663 (1997).
11 Saint, N., Marri, L., Marchini, D. & Molle, G. The antibacterial peptide ceratotoxin A displays alamethicin-like behavior in lipid bilayers. *Peptides* 24, 1779-1784, doi:http://dx.doi.orq/10.1016/j.peptides.2003.09.015 (2003).
12 Majd, S. et al. Applications of biological pores in nanomedicine, sensing, and nanoelectronics. *Current Opinion in Biotechnology* 21, 439-476, doi:http://dx-.doi.orq/10.1016/j.copbio.2010.05.002 (2010).
13 Montal, M. & Mueller, P. Formation of bimolecular membranes from lipid monolayers and a study of their electrical properties. *Proceedings of the National Academy of Sciences* 69, 3561-3566 (1972).
14 Stahl, E., Martin, T. G., Praetorius, F. & Dietz, H. Facile and Scalable Preparation of Pure and Dense DNA Origami Solutions. *Angewandte Chemie International Edition* 53, 12735-12740, doi:doi:10.1002/anie.201405991 (2014).

What is claimed is:

1. A hybrid pore-forming compound, comprising:
   a pore-forming peptide having a first terminus and a second terminus, wherein a first oligonucleotide is linked to the first terminus, wherein the first oligonucleotide is derived from DNA, RNA, LNA, BNA, or PNA, wherein a first functional moiety is linked to the second terminus, and wherein the first functional moiety is hydrophilic,
   wherein the pore-forming peptide comprises a Ceratotoxin A (CtxA),
   wherein the first oligonucleotide comprises a single strand oligonucleotide, and
   wherein the first functional moiety comprises a polythymine strand.

2. The compound according to claim 1, wherein a second functional moiety is linked to a second oligonucleotide that is hybridized to the first oligonucleotide bonded to the first terminus of the peptide, wherein the second oligonucleotide is derived from DNA, RNA, LNA, BNA, or PNA, wherein the second functional moiety is a hydrophobic membrane binder, receptor, drug molecule, antibody, aptamer, metabolite, or fluorescent marker.

3. The compound according to claim 2, wherein the hydrophobic membrane binder is present and comprises a cholesterol moiety.

4. The compound according to claim 1, wherein a template strand having a plurality of complementary hybridization sites is hybridized to a portion of the first oligonucleotide linked to the first terminus.

5. The compound according to claim 1, wherein a plurality of the pore-forming peptides are present with each first oligonucleotide linked to the first terminus hybridized to a template strand, such that the compound forms a larger pore.

6. The compound according to claim 1, wherein a plurality of the pore-forming peptide are present with each first oligonucleotide linked to the first terminus hybridized to the template strand such that the compound has a tetrameric, hexameric, octameric or dodecameric pore conformation.

7. The compound according to claim 1, wherein the peptide is functionalized differently at the first terminus as compared to the second terminus.

8. A method for forming the hybrid pore-forming compound according to claim 1, comprising the steps of:

obtaining i) the pore-forming peptide, ii) the first oligonucleotide and iii) the first functional moiety; and forming the pore-forming compound by self-assembly of i), ii), iii).

9. The method according to claim 8, further including the step of reacting in solution a template strand having a plurality of complimentary hybridization sites with an excess of the pore-forming compounds comprising the i), ii), iii);

removing excess unreacted pore-forming compounds by high pressure liquid chromatography.

10. The method according to claim 9, further including the step of hybridizing the first oligonucleotide to a second oligonucleotide, wherein the second oligonucleotide is present in an excess amount as compared to the first oligonucleotide.

11. A membrane, comprising a substrate and the compound according to claim 1, wherein the compound provides a pore between a first side of the substrate and a second side of the substrate.

12. The compound according to claim 1, wherein an extended, nucleic acid nanostructure serves as a template for assembling a plurality of pore formers into a pore, wherein the nucleic acid nanostructure contains a second functional moiety directly attached thereto, and wherein the nucleic acid nanostructure is a DNA origami structure or a single stranded tile assembly or a RNA origami structure.

13. The compound according to claim 3, wherein a template strand having 4, 6, 8, or 12 complementary hybridization sites is hybridized to a portion of the first oligonucleotide linked to the first terminus.

14. The compound according to claim 13, wherein a plurality of the pore-forming peptides are present with each first oligonucleotide linked to the first terminus hybridized to the template strand, such that the compound forms a larger pore, or wherein a plurality of the pore-forming peptide are present with each first oligonucleotide linked to the first terminus hybridized to the template strand such that the compound has a tetrameric, hexameric, octameric or dodecameric pore conformation.

15. The compound according to claim 14, wherein a second membrane binder is linked to the third oligonucleotide to aid in stabilizing a pore formed by the compound, and wherein the peptide is functionalized differently at the first terminus as compared to the second terminus.

16. A method for forming the hybrid pore-forming compound according to claim 15, comprising the steps of:

obtaining i) the pore-forming peptide, ii) the first oligonucleotide and iii) the first functional moiety; and forming the pore-forming compound by self-assembly of i), ii), iii).

17. A membrane, comprising a substrate and the compound according to claim 15, wherein the compound provides a pore between a first side of the substrate and a second side of the substrate.

18. The compound according to claim 1, wherein a template strand having a plurality of complementary hybridization sites is hybridized to a portion of the first functional moiety linked to the second terminus.

19. A pore formed by the compound according to claim 3.

20. The pore according to claim 19, wherein a first template strand having a plurality of complementary hybridization sites is hybridized to a portion of the first oligonucleotide linked to the first terminus, and a second template strand having a plurality of complementary hybridization sites is hybridized to a portion of the first functional moiety linked to the second terminus.

21. The pore according to claim 20, wherein a plurality of the pore-forming peptides are present with each first oligonucleotide linked to the first terminus hybridized to the template strand and each first functional moiety linked to the second terminus hybridized to the second template strand.

* * * * *

UNITED STATES PATENT AND TRADEMARK OFFICE
CERTIFICATE OF CORRECTION

| | | |
|---|---|---|
| PATENT NO. | : 12,281,178 B2 | Page 1 of 1 |
| APPLICATION NO. | : 17/278765 | |
| DATED | : April 22, 2025 | |
| INVENTOR(S) | : Aziz Fennouri, Jonathan List and Michael Mayer | |

It is certified that error appears in the above-identified patent and that said Letters Patent is hereby corrected as shown below:

On the Title Page

Item [54], and in the Specification, Column 1, Lines 1-4 The title should read:
OLIGONUCLEOTIDE-BASED TUNING OF PORE-FORMING PEPTIDES FOR INCREASING PORE SIZE, MEMBRANE AFFINITY, STABILITY, AND ANTIMICROBIAL ACTIVITY Signed and Sealed this
Twenty-seventh Day of January, 2026

John A. Squires
*Director of the United States Patent and Trademark Office*

SEQUENCE LISTING

```
<160> NUMBER OF SEQ ID NOS: 197

<210> SEQ ID NO 1
<211> LENGTH: 36
<212> TYPE: PRT
<213> ORGANISM: Artificial Sequence
<220> FEATURE:
<223> OTHER INFORMATION: Synthetic peptide

<400> SEQUENCE: 1

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro Val Ala Ala
            20                  25                  30

Gly Leu Val Gly
        35

<210> SEQ ID NO 2
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 2
tttttcagca atttaagatc cacccacgtt tttgtcactt ccgcgcacca gtttt         55

<210> SEQ ID NO 3
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 3
```

-continued

```
ttttacgtgg gtggatctta aattgctgat ttt                                  33

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
ctggtgcgcg gaagtgactt tt                                              22

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 5
gcagaagccg cctgcaacag tgagatct                                        28

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 6
taagaatata gtgagagcaa aagaagat                                        28

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 7
ttatagtggg tgcctaatga gtgagctt                                        28

<210> SEQ ID NO 8
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 8
ttaaatccct tataaatcgg ttccgaaatc ggcatt                               36

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 9
ttaccagtaa taaagggat tcaccagtca cacgtt                                36

<210> SEQ ID NO 10
<211> LENGTH: 42
<212> TYPE: DNA
<213> ORGANISM: Artificial Sequence
```

-continued

```
<220> FEATURE:
<223> OTHER INFORMATION: Synthetic oligonucleotide

<400> SEQUENCE: 10
ggaagcctcc acactcgcta tgcactccag gaacgccatc aa                              42

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 11
atttatccaa tccattatcc ggtattctaa aataa                                     35

<210> SEQ ID NO 12
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 12
ttcattgaat cccttaaac aattgcataa gcatagggcg at                              42

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 13
ctcaaactca tcgagaacaa gttaaacc                                             28

<210> SEQ ID NO 14
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 14
gcttcaactt caaatccaag aacgggta                                             28

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 15
tatcgcgtta tcatatgcgt ttcggctgtc tttccgtagg aa                              42

<210> SEQ ID NO 16
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 16
gtcagtttac gtggcacaga cgaacaaacg gcgtacctac at                              42
```

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 17
ttttataatc agtgaggcca ccgagataag ag                                    32

<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 18
aaaagaatag cccgccggaa agcaactgag agaatcgatg aa                         42

<210> SEQ ID NO 19
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 19
caaaatattt ttattttcat cttatcat                                        28

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
aatattttca atcaatatct gcctttgc                                        28

<210> SEQ ID NO 21
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 21
ctcaacaaat ttttagaacc ctcatatt                                        28

<210> SEQ ID NO 22
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 22
acaataaatt agttaatctt accaacgctg taaatatatt tt                         42

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

```
<400> SEQUENCE: 23
gttgagtgtt gttctttccg gcggtgcgcc tgaga                                35

<210> SEQ ID NO 24
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 24
tagagctgcg cgtactatgg tcgttaga                                       28

<210> SEQ ID NO 25
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 25
aataaccaag gcaaagaatt aggagcgg                                       28

<210> SEQ ID NO 26
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 26
agccctaaaa tctaaagcat ctatcatttt taaattaatg cc                       42

<210> SEQ ID NO 27
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 27
ttttagagcc gtcaatagac taacaactaa tagatt                              36

<210> SEQ ID NO 28
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 28
tgcgtaggca cgtaaaacag aaaaattcta ctaatagtag taaattcat                49

<210> SEQ ID NO 29
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 29
aattatctta ttaacaaacc cttgaatggc tattaaaccc gt                       42

<210> SEQ ID NO 30
```

<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 30
ggttgataat cagagcaaac attgggaa                                    28

<210> SEQ ID NO 31
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 31
ttaacctacc atatcaaaat aatggaaggg ttagtt                            36

<210> SEQ ID NO 32
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 32
agatagggcg aaaatcctgt ttgatggt                                    28

<210> SEQ ID NO 33
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 33
ccggcttcta atttccgact tgcgggagga acgcg                             35

<210> SEQ ID NO 34
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 34
tattaaaaga gagttgcagc aagctgca                                    28

<210> SEQ ID NO 35
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 35
ttagtttgac cattgatgaa acaaacatac agtgccc                           37

<210> SEQ ID NO 36
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 36
aactatataa cgagagcctt aaatcaagac aacat                35

<210> SEQ ID NO 37
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 37
tttcgccatt caggctgccc aggcaaagcg ccattt               36

<210> SEQ ID NO 38
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 38
acgacgtgat ccccgggtac ccgctcaa                        28

<210> SEQ ID NO 39
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 39
ggaaacgata ccaagcgcgg acagcctttc gag                  33

<210> SEQ ID NO 40
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 40
gagagacaaa cagccgaggc gttttagcat agatatttaa ca        42

<210> SEQ ID NO 41
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 41
ttagtaacag tacctttac atcggcaaat ccaatcgcaa gacatt     46

<210> SEQ ID NO 42
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 42
tagtaatacc gttggaggcc gattaaag                        28

<210> SEQ ID NO 43
<211> LENGTH: 42
<212> TYPE: DNA

```
<213> ORGANISM: Artificial Sequence
<220> FEATURE:
<223> OTHER INFORMATION: Synthetic oligonucleotide

<400> SEQUENCE: 43
tcacaatcga agaagcgaa caattttctt tgaattacct tt                    42

<210> SEQ ID NO 44
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 44
aatcatgttc ttactaatta cttaagacgc tgaga                           35

<210> SEQ ID NO 45
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 45
acgaaggcac caaccttaaa cg                                         22

<210> SEQ ID NO 46
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 46
cgttctagct gagcggaaca aggaatca                                   28

<210> SEQ ID NO 47
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 47
ttaaagtaat tctgtccaag taccgacaaa aggttt                          36

<210> SEQ ID NO 48
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 48
gtaagaaggc aaatcaacag tattcgac                                   28

<210> SEQ ID NO 49
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 49
gttttgacgt ctttccagag caggttgg                                   28
```

<210> SEQ ID NO 50
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 50
agatacataa gcaataaagc ctcagagc                               28

<210> SEQ ID NO 51
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 51
acattctata tctttaggag cataatacat ttgag                        35

<210> SEQ ID NO 52
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 52
ttccaatact gcggaatcgt caatgacc                                28

<210> SEQ ID NO 53
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 53
aagccaagag ctcggggttt tcgcatcgtg tgagcgagta ac                42

<210> SEQ ID NO 54
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 54
tttgataaga ggtcattttt gagtgaataa ccgggtaat                    39

<210> SEQ ID NO 55
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 55
aagtgtaact gcccgctttc cccagcag                                28

<210> SEQ ID NO 56
<211> LENGTH: 42
<212> TYPE: DNA
<213> ORGANISM: Artificial Sequence
<220> FEATURE:

<223> OTHER INFORMATION: Synthetic oligonucleotide

<400> SEQUENCE: 56
tcaaaaggaa gcctgtacgg tgtctggatt taatgcgtcg ct                42

<210> SEQ ID NO 57
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 57
aacgccaaat tcgttgggcg ccagggtggt ttttataacg tgctttcct        49

<210> SEQ ID NO 58
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 58
gtgaatttaa ggctccaaaa ggagcattta ac                          32

<210> SEQ ID NO 59
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 59
aaaggtggca tctaaagaaa tgattcgc                               28

<210> SEQ ID NO 60
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 60
cttctgaatt atttattttc aggtttaacg tcagatgaat atactt           46

<210> SEQ ID NO 61
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 61 gtaccccctaa attgtaaacg ttaatatt                              28

<210> SEQ ID NO 62
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 62
ttggtgtccc taaaacgagc acgtcttttc accag                       35

```
<210> SEQ ID NO 63
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 63
tagcaatact gcatgcctgc aatcagagcg ggagc                          35

<210> SEQ ID NO 64
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 64
caaaagcggt cagtgtcatt gggcctct                                  28

<210> SEQ ID NO 65
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 65
gaacctcgcc agttacaaaa ttaccttttg aaatatatca gaattaaat           49

<210> SEQ ID NO 66
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 66
agggaaggcg taaccaccac aggattttca tcacg                          35

<210> SEQ ID NO 67
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 67
cccgccggtg gcgagaaagg accattgcct tgcctagact tt                  42

<210> SEQ ID NO 68
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 68
acgtcaagcc cttcaccgcc taacgcgcgg ggagaggcgg tt                  42

<210> SEQ ID NO 69
<211> LENGTH: 35
<212> TYPE: DNA
<213> ORGANISM: Artificial Sequence
<220> FEATURE:
<223> OTHER INFORMATION: Synthetic oligonucleotide
```

<400> SEQUENCE: 69
tgttttaaat atgcatcaat atatgtgcgg atggc    35

<210> SEQ ID NO 70
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 70
gtctttatga acctcaaata tttttaaa    28

<210> SEQ ID NO 71
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 71
ccgaccgcgc cataagtcct gaacaaga    28

<210> SEQ ID NO 72
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 72
ttaagaacgc gagaaaactt taatataaga cgacg    35

<210> SEQ ID NO 73
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 73
gaacaagagt ccacgaagat ctacgccaac aaagg    35

<210> SEQ ID NO 74
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 74
atcgcccagc agggagttaa tgataa    26

<210> SEQ ID NO 75
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 75
gcactaaatc ggaaagatgg gcccagtcag tttga    35

<210> SEQ ID NO 76
<211> LENGTH: 23

```
<212> TYPE: DNA
<213> ORGANISM: Artificial Sequence
<220> FEATURE:
<223> OTHER INFORMATION: Synthetic oligonucleotide

<400> SEQUENCE: 76
acggggtcag gtttatcagc ttg                                            23

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 77
agtctctggg taaaatacgt aatgc                                          25

<210> SEQ ID NO 78
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 78
taaagatgtc tggaaaagcc caagattgta taagctgtta aatctggtg                49

<210> SEQ ID NO 79
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 79
caccgcttca gctcattttt taaccaatag ccagc                               35

<210> SEQ ID NO 80
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 80
ggcgaaccgc ttaatgcgcc gtaaacag                                       28

<210> SEQ ID NO 81
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 81
aactaaatta tttcaacgca agtgtagg                                       28

<210> SEQ ID NO 82
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 82
```

```
ttttgttagc aaatcagata tttacgag                                              28

<210> SEQ ID NO 83
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 83
gagacagccc tgtattccat ataacagtaa tttcacctta ga                             42

<210> SEQ ID NO 84
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 84
cagtgccaag ctttctttga taactcgt                                              28

<210> SEQ ID NO 85
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 85
acaaacatga aggtctgac ctgaaagctt tgacgaaaac gc                              42

<210> SEQ ID NO 86
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 86
ttcatttcat ccaataaatc a                                                     21

<210> SEQ ID NO 87
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 87
aaaatactga gagccagcag cggagaggtg caaggctgtt tcctgtgtg                      49

<210> SEQ ID NO 88
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 88
tctgacccaa tataatcctg attgtttgga ttatagattt ag                             42

<210> SEQ ID NO 89
<211> LENGTH: 42
<212> TYPE: DNA
<213> ORGANISM: Artificial Sequence
```

-continued

```
<220> FEATURE:
<223> OTHER INFORMATION: Synthetic oligonucleotide

<400> SEQUENCE: 89
ggtcgactga gaattgtgat ataggtctaa ttattcattt ca                    42

<210> SEQ ID NO 90
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 90
ttctacaatt ttatcctggc tattttgcac ccagtt                           36

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
agtttcaata cttttgcggg a                                           21

<210> SEQ ID NO 92
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 92
cagaagcaga gtacctttaa ttgctccttt tt                               32

<210> SEQ ID NO 93
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 93
tttaggccaa attaaacatc aaacaggact caatcgtctg aa                    42

<210> SEQ ID NO 94
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 94
caaaagaagt tttgccagag gttgcttcca ggtca                            35

<210> SEQ ID NO 95
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 95
gctggcgtat ccgcttaatg aatcggcc                                    28
```

<210> SEQ ID NO 96
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 96
cagtttgcac gctggtttgc cagtcgggga gccgg        35

<210> SEQ ID NO 97
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 97
tctatcatga gacgggcaac atgcgtat        28

<210> SEQ ID NO 98
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 98
tacaaactcc atcgttgacc cccagtagca a        31

<210> SEQ ID NO 99
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 99
tcattaccgc gccctcaata aatacaaa        28

<210> SEQ ID NO 100
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 100
cgttaaacag taggtatccc atcctaat        28

<210> SEQ ID NO 101
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 101
accagaagca aaattttcgc aaatggtcat tacct        35

<210> SEQ ID NO 102
<211> LENGTH: 36
<212> TYPE: DNA
<213> ORGANISM: Artificial Sequence
<220> FEATURE:
<223> OTHER INFORMATION: Synthetic oligonucleotide

```
<400> SEQUENCE: 102
gaggcgcaga cagcaaaatg tatcatcgcc aggccg                                    36

<210> SEQ ID NO 103
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 103
gctgattagg gcgaaaaacc ggcatctggt tgggt                                     35

<210> SEQ ID NO 104
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 104
caaaaagact ccaatgtaaa tgaaacagta cataa                                     35

<210> SEQ ID NO 105
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 105
caagccggcg agaggctttt gattaattca gaccg                                     35

<210> SEQ ID NO 106
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 106
gcttaattct agagtgtaaa aggtcacgcg gattctccgt gg                             42

<210> SEQ ID NO 107
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 107
aaattgtaaa ggggagtatc gtcgcgtctg gcctt                                     35

<210> SEQ ID NO 108
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 108
taaatttcat gtaacctgtt tatcaaca                                             28

<210> SEQ ID NO 109
```

```
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 109
ttgctggcaa gtgtagcggt ccgccagaat cctgagaagt gttttt          46

<210> SEQ ID NO 110
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 110
agaaggcaat aagaaacgat tagagtcaaa acacc                       35

<210> SEQ ID NO 111
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 111
tgatggcgca ttaagggcg cgagctgata ccaag                        35

<210> SEQ ID NO 112
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 112
aagaacgcat attatttatc caaaatcaaa taagg                       35

<210> SEQ ID NO 113
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 113
aaggccgcta tcagattaac aataaaacag aggtgagaca gg               42

<210> SEQ ID NO 114
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 114
agtagatata aagctaaatc gattcaac                               28

<210> SEQ ID NO 115
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 115
```

```
atctaaaggc aacagagat aatggattcc gccag                            35

<210> SEQ ID NO 116
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 116
gtcatagcga ttaaccagtt tccagctttc atcaa                           35

<210> SEQ ID NO 117
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 117
agaaaccgta acataccttg catgcgcgaa ctgatcatta aataaccgt            49

<210> SEQ ID NO 118
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 118
gagtagagtc tgtcagacag gaacggta                                   28

<210> SEQ ID NO 119
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 119
ttagcatgtc aatcatatcg gtaatcgtaa aacttt                          36

<210> SEQ ID NO 120
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 120
atcatattac aggctgttta gctatattag aggcg                           35

<210> SEQ ID NO 121
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 121
taattacctt taattgtatc gtgccttgag tacaagaaa                       39

<210> SEQ ID NO 122
<211> LENGTH: 35
<212> TYPE: DNA
```

```
<213> ORGANISM: Artificial Sequence
<220> FEATURE:
<223> OTHER INFORMATION: Synthetic oligonucleotide

<400> SEQUENCE: 122
ataaataagt aaaatgttta gactggatag cgttt                                    35

<210> SEQ ID NO 123
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 123
ttgtctttac cctgactaat aaatcaaaaa tcagtt                                   36

<210> SEQ ID NO 124
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 124
ctacaggtga cggggaaagc ctcatggaaa gattgaccgt aa                            42

<210> SEQ ID NO 125
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 125
tttaactcac attaattgcg ttgcgctcaa gcctg                                    35

<210> SEQ ID NO 126
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 126
acgctgcaaa gcgaaaggag cgggcgctag ggctt                                    35

<210> SEQ ID NO 127
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 127
tgattcccaa aaacattatg atcaaatc                                            28

<210> SEQ ID NO 128
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 128
aaaaatggct tagatagaaa aagcctgttt agtttaattc gaaccatca                     49
```

```
<210> SEQ ID NO 129
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 129
gccagtataa aagaagaact caatattaat ttacattggc ag                         42

<210> SEQ ID NO 130
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 130
ggtgagagaa gcaaattaag aaagtaccgc atgct                                 35

<210> SEQ ID NO 131
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 131
atatgatgtt gtaccaattc tgcgaacgac aaaatagcga ta                         42

<210> SEQ ID NO 132
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 132
agaggcattc atctgttata tctgattgct ttgaa                                 35

<210> SEQ ID NO 133
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 133
ttcaaatgct gatggagaaa caataacg                                         28

<210> SEQ ID NO 134
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 134
agttaatttt tcgagttcag ctaatgca                                         28

<210> SEQ ID NO 135
<211> LENGTH: 28
<212> TYPE: DNA
<213> ORGANISM: Artificial Sequence
<220> FEATURE:
```

```
<223> OTHER INFORMATION: Synthetic oligonucleotide

<400> SEQUENCE: 135
gaaccctaat tgaggaaggt taagtatt                                              28

<210> SEQ ID NO 136
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 136
ggccctggaa cgtggactcc acgacgacga tgtgcgtagc ta                              42

<210> SEQ ID NO 137
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 137 tttttgtta aaattcgcat taaattttaa atatt                                       35

<210> SEQ ID NO 138
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 138
ggattagaaa gcgggttcag aaaacgag                                              28

<210> SEQ ID NO 139
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 139
tttggtaata tccagaacaa actatcggcc ttgctt                                     36

<210> SEQ ID NO 140
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 140
aaatgaaaaa catcgccatt acctgtagga gggga                                      35

<210> SEQ ID NO 141
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 141
aacatacaaa cctgtcgtgc cagcggtc                                              28
```

<210> SEQ ID NO 142
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 142
tgctttgggg agcccccgat tgggatacg acggcccgaa cg                          42

<210> SEQ ID NO 143
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 143
tttattttaa atgcaatgcc tgagtaatgg ataaa                                 35

<210> SEQ ID NO 144
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 144
tttttgagcc acgccgaacg aaccaccaaa ataatgcctc ag                         42

<210> SEQ ID NO 145
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 145
acgccaaaat ggttttaacc tttacaaaat cgcgc                                 35

<210> SEQ ID NO 146
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 146
aaaatagcag acgataaaaa catccttgaa aacat                                 35

<210> SEQ ID NO 147
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 147
ttgaatataa tgctgtagtt agagcttaat tgcttt                                36

<210> SEQ ID NO 148
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 148
cagtatacat gtagaaacca aaatagcata acgtccataa aaac        44

<210> SEQ ID NO 149
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 149
caagaaacac caccctcccc ctttccctca gagcagccac c        41

<210> SEQ ID NO 150
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 150
aaaggaatgt ctttccagac gttattgcga ataataattt        40

<210> SEQ ID NO 151
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 151
cgggagaatg taacactaat cagcactaaa acactttgag        40

<210> SEQ ID NO 152
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 152
gcaacactgc gtaaccatta ccaagtacaa cgggtcacc        39

<210> SEQ ID NO 153
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 153
caaagtcaag cccaataagt ttaaagaggc aaattcatg        39

<210> SEQ ID NO 154
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 154
tatcttaccc gtactcaatc tttccaccac cggagccacc a        41

<210> SEQ ID NO 155
<211> LENGTH: 34

```
<212> TYPE: DNA
<213> ORGANISM: Artificial Sequence
<220> FEATURE:
<223> OTHER INFORMATION: Synthetic oligonucleotide

<400> SEQUENCE: 155
attgagttag aaccgccggc atccctcaga cact                              34

<210> SEQ ID NO 156
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 156
aacaaataaa tcctccgggg ttttccaccc tcaagcccaa t                      41

<210> SEQ ID NO 157
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 157
attaaagcca gaatggaaag cgctcctcaa gaagagccac agagataac              49

<210> SEQ ID NO 158
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 158
taccacattc aactaataat tttctcggaa cattgt                            36

<210> SEQ ID NO 159
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 159
cagtatacat gtagaaacca aaatagcata acgtccataa aaac                   44

<210> SEQ ID NO 160
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 160
gacgattggc cttgataagt gcctagtacc gatgaaata                         39

<210> SEQ ID NO 161
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 161
```
aatttaccgt tccagcatga aaggatagca                                    30

<210> SEQ ID NO 162
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 162
attttgctaa acaactttat aggtgtatca cgaagccc                           38

<210> SEQ ID NO 163
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 163
tttttaaatc agttgagatt taggaattac aggtagaaag attcgaaaag              50

<210> SEQ ID NO 164
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 164
gtcgaagagg cttcgcataa ccgatatatt agcattgaca ggaggttgag              50

<210> SEQ ID NO 165
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 165
gagccgccgc ccggtcgcta tccgcgacca ccggaa                             36

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
cgctgttcct cacgataatt                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 167
tttagcttcc ataccacctg                                               20

<210> SEQ ID NO 168
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 168
atcggaacga gggcgatttc accagtgaat tcaggtggta tggaagcta                49

<210> SEQ ID NO 169
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 169
cttaaacctc agcagcgaaa aaacaattag cccgacttca ggtggtatgg aagcta         56

<210> SEQ ID NO 170
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 170
accgccaccc tcagcgccat ttcgggttta ttcaggtggt atggaagcta                50

<210> SEQ ID NO 171
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 171
aagttttacg gctacagagg ctcatctata gcaggaaatt ttcaggtggt atggaagcta    60

<210> SEQ ID NO 172
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 172
tattcacaac cctcagagcc accgccatta gcaatagatt caggtggtat ggaagcta      58

<210> SEQ ID NO 173
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 173
caccctcaga ctgtagcgcg acaaattcag gtggtatgga agcta                    45

<210> SEQ ID NO 174
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 174
tgatacagga ctaaagactt tagaatatag cgacgaaggt ttcaggtggt atggaagcta    60

<210> SEQ ID NO 175
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 175
taagcgtcag gaagtttcca taaaacggcc tttacaaccg ttcaggtggt atggaagcta    60

<210> SEQ ID NO 176
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 176
ttgcgccctt ttgcgggatc agatttcacc aggggaattt caggtggtat ggaagcta    58

<210> SEQ ID NO 177
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 177
ggaagaaaaa tctaccgcat agtagagccg gtcaatcatt tcaggtggta tggaagcta    59

<210> SEQ ID NO 178
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 178
gcaggtcaga accaccacca ccagagtcat aatttatttt caggtggtat ggaagcta    58

<210> SEQ ID NO 179
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 179
agacgccttt acagacttat gcgattttaa caagaactta tcattcaggt ggtatggaag    60
cta    63

<210> SEQ ID NO 180
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 180
aacgaactaa cggaacaacg gtaagggttc aggtggtatg gaagcta    47

<210> SEQ ID NO 181
<211> LENGTH: 48
<212> TYPE: DNA
<213> ORGANISM: Artificial Sequence

```
<220> FEATURE:
<223> OTHER INFORMATION: Synthetic oligonucleotide

<400> SEQUENCE: 181
gcaataataa cggaatacgt agccagcgtt caggtggtat ggaagcta        48

<210> SEQ ID NO 182
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 182
tcattatacc agtcatcatc aattgagctt caggtggtat ggaagcta        48

<210> SEQ ID NO 183
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 183
ttgggcttga gatggagctg caaatattca ggtggtatgg aagcta          46

<210> SEQ ID NO 184
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 184
taagcagata gccgaagaaa cttgtcttca ggtggtatgg aagcta          46

<210> SEQ ID NO 185
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 185
agaactggca tgattattac gcagggcgtt caggtggtat ggaagcta        48

<210> SEQ ID NO 186
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 186
taccagaagg aaaccgaaag gtaaattttc aggtggtatg gaagcta         47

<210> SEQ ID NO 187
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 187
caactttaat cattgaccca aattcattca ggtggtatgg aagcta          46
```

<210> SEQ ID NO 188
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 188
gagggtaaga aacaccagaa cgaaaggcta ttgagttcag gtggtatgga agcta    55

<210> SEQ ID NO 189
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 189
gagtgtactg gtaatgtata aactcaccag agggaagctt ttatcgtgag gaacagcg    58

<210> SEQ ID NO 190
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 190
atacatggct tttgatattt cggatgtacc taactgaatt ttatcgtgag gaacagcg    58

<210> SEQ ID NO 191
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 191
gacaatgaca acaaccctaa aggaagtaaa tggcagatac ttttatcgtg aggaacagcg    60

<210> SEQ ID NO 192
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 192
agcttgatac cgatagtttc acgtgttttg tctacgaggc ttttatcgtg aggaacagcg    60

<210> SEQ ID NO 193
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 193
ccgtcaaagg ccacagccct catagttaat cataacctttt tatcgtgagg aacagcg    57

<210> SEQ ID NO 194
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 194
attaaagcca gaatggaaag cgctcctcaa gaagagccac agagataact tttatcgtga     60
ggaacagcg                                                             69

<210> SEQ ID NO 195
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 195
aacaaataaa tcctccgggg ttttccaccc tcaagcccaa tttttatcgt gaggaacagc     60
g                                                                     61

<210> SEQ ID NO 196
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 196
gacgattggc cttgataagt gcctagtacc gatgaaatat tttatcgtga ggaacagcg      59

<210> SEQ ID NO 197
<211> LENGTH: 7249
<212> TYPE: DNA
<213> ORGANISM: Artificial Sequence
<220> FEATURE:
<223> OTHER INFORMATION: Synthetic oligonucleotide

<400> SEQUENCE: 197
aatgctacta ctattagtag aattgatgcc accttttcag ctcgcgcccc aaatgaaaat     60
atagctaaac aggttattga ccatttgcga atgtatcta atggtcaaac taaatctact    120
cgttcgcaga attgggaatc aactgttata tggaatgaaa cttccagaca ccgtacttta    180
gttgcatatt taaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tcttttgat gcaatccgct tgcttctga ctataatagt    420 cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080

```
gtctgcgcct cgttccggct aagtaacatg gagcaggtcg cggatttcga cacaatttat    1140
caggcgatga tacaaatctc cgttgtactt tgtttcgcgc ttggtataat cgctgggggt    1200
caaagatgag tgttttagtg tattcttttg cctctttcgt tttaggttgg tgccttcgta    1260
gtggcattac gtattttacc cgtttaatgg aaacttcctc atgaaaaagt ctttagtcct    1320
caaagcctct gtagccgttg ctaccctcgt tccgatgctg tctttcgctg ctgagggtga    1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
ttttggagat tttcaacgtg aaaaaattat tattcgcaat cctttagtt gttcctttct    1620 attctcactc cgctgaaact gttgaaagtt gtttagcaaa atcccataca gaaaattcat    1680
ttactaacgt ctggaaagac gacaaaactt tagatcgtta cgctaactat gagggctgtc    1740
tgtggaatgc tacaggcgtt gtagtttgta ctggtgacga aactcagtgt tacggtacat    1800
gggttcctat tgggcttgct atccctgaaa atgagggtgg tggctctgag gtggcggtt    1860 ctgagggtgg cggttctgag ggtggcggta ctaaacctcc tgagtacggt gatacaccta    1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcagggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgagggag gcggttccgg tggtggctct ggttccggtg    2400
attttgatta tgaaaagatg gcaaacgcta ataaggggc tatgaccgaa atgccgatg    2460 aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt ccttctggt aactttgttc ggctatctgc ttacttttct    2940 taaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
```

```
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttaccty    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc tttttctagt aattatgatt    3840
ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta aagatatttt agataaccty cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttaatgg cgatgtttta    4980 gggctatcag ttcgcgcatt aaagactaat agccattcaa aaatattgtc tgtgccacgt    5040
attcttacgc tttcaggtca gaagggttct atctctgttg gccagaatgt cccttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400 atcccttta tcggcctcct gtttagctcc cgctctgatt ctaacgagga agcacgtta    5460 tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt cccgtcaag ctctaaatcg    5640 ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
```

```
-continued tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctcccgc gcgttggccg attcattaat gcagctggca     6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360
atcccccttt cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac tgtcgtcgtc ccctcaaact    6540
ggcagatgca cggttacgat gcgcccatct acaccaacgt gacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa tgcgaatttt aacaaaatat taacgtttac    6780
aatttaaata tttgcttata caatcttcct gttttggggg cttttctgat tatcaaccgg    6840
ggtacatatg attgacatgc tagttttacg attaccgttc atcgattctc ttgtttgctc    6900
cagactctca ggcaatgacc tgatagcctt tgtagatctc tcaaaaatag ctaccctctc    6960
cggcattaat ttatcagcta gaacggttga atatcatatt gatggtgatt tgactgtctc    7020
cggcctttct cacccttttg aatctttacc tacacattac tcaggcattg catttaaaat    7080
atatgagggt tctaaaaatt tttatccttg cgttgaaata aaggcttctc ccgcaaaagt    7140
attacagggt cataatgttt ttggtacaac cgatttagct ttatgctctg aggctttatt    7200
gcttaatttt gctaattctt tgccttgcct gtatgattta ttggatgtt                7249
```